(12) United States Patent
Manifold et al.

(10) Patent No.: US 7,704,601 B2
(45) Date of Patent: Apr. 27, 2010

(54) FIBROUS STRUCTURES

(75) Inventors: John Allen Manifold, Milan, IN (US); Charles Chidozie Ekenga, Cincinnati, OH (US); Douglas Jay Barkey, Hamilton Township, OH (US); Kathleen Diane Sands, West Chester, OH (US); Thorsten Knobloch, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 132 days.

(21) Appl. No.: 12/040,733

(22) Filed: Feb. 29, 2008

(65) Prior Publication Data

US 2009/0218058 A1 Sep. 3, 2009

(51) Int. Cl.
*B32B 5/16* (2006.01)

(52) U.S. Cl. ............... 428/326; 162/112; 162/123; 162/135

(58) Field of Classification Search ............ 162/231, 162/112, 123, 135; 428/326, 113
See application file for complete search history.

(56) References Cited

U.S. PATENT DOCUMENTS

| | | | |
|---|---|---|---|
| 3,974,025 A | 8/1976 | Ayers | |
| 5,804,281 A | 9/1998 | Phan et al. | |
| 6,165,319 A | 12/2000 | Heath et al. | |
| 6,797,114 B2 | 9/2004 | Hu | |
| 7,494,563 B2 | 2/2009 | Edwards et al. | |
| 2004/0023003 A1 | 2/2004 | Basler et al. | |
| 2004/0112783 A1 | 6/2004 | Mukai et al. | |
| 2004/0258887 A1 | 12/2004 | Maciag et al. | |
| 2004/0261639 A1 | 12/2004 | Vaughn et al. | |
| 2005/0045293 A1* | 3/2005 | Hermans et al. ............ 162/109 |
| 2005/0067126 A1 | 3/2005 | Horenziak et al. | |
| 2005/0178513 A1 | 8/2005 | Russell et al. | |
| 2008/0041543 A1 | 2/2008 | Dyer et al. | |
| 2008/0260996 A1 | 10/2008 | Heilman et al. | |

FOREIGN PATENT DOCUMENTS

| | | |
|---|---|---|
| EP | 1 876 291 A2 | 1/2005 |
| GB | 2319539 A | 5/1998 |
| WO | WO 96/33310 A1 | 10/1996 |
| WO | WO 97/17494 A1 | 5/1997 |
| WO | WO 98/44194 A1 | 10/1998 |
| WO | WO 2005/068720 A1 | 7/2005 |
| WO | WO 2005/080683 A2 | 9/2005 |
| WO | WO 2006/060814 A2 | 6/2006 |
| WO | WO 2007/001576 A1 | 1/2007 |
| WO | WO 2007/070124 A1 | 6/2007 |

OTHER PUBLICATIONS

U.S. Appl. No. 12/040,637, filed Feb. 29, 2008, Manifold, et al.

(Continued)

*Primary Examiner*—Eric Hug
*Assistant Examiner*—Jacob Thomas Minskey
(74) *Attorney, Agent, or Firm*—C. Brant Cook

(57) ABSTRACT

Fibrous structures that exhibit a cross machine direction total energy absorption (CDTEA) of greater than 8 cm-g/cm$^2$ as measured according to the TEA Test Method.

29 Claims, 8 Drawing Sheets

OTHER PUBLICATIONS

U.S. Appl. No. 12/040,662, filed Feb. 29, 2008, Manifold, et al.
U.S. Appl. No. 12/040,692, filed Feb. 29, 2008, Manifold, et al.
U.S. Appl. No. 12/040,701, filed Feb. 29, 2008, Manifold, et al.
U.S. Appl. No. 12/040,715, filed Feb. 29, 2008, Manifold, et al.
U.S. Appl. No. 12/040,723, filed Feb. 29, 2008, Manifold, et al.
International Search Report Mailed May 10, 2009.
U.S. Office Action -U.S. Appl. No. 12/040,692, Sep. 8, 2009.
U.S. Office Action -U.S. Appl. No. 12/040,701, Sep. 9, 2009.
U.S. Office Action -U.S. Appl. No. 12/040,715, Sep. 16, 2009.
U.S. Office Action -U.S. Appl. No. 12/040,723, Sep. 8, 2009.
U.S. Office Action—U.S. Appl. No. 12/040,733, Sep. 8, 2009.

* cited by examiner

FIBROUS STRUCTURES

FIELD OF THE INVENTION

The present invention relates to fibrous structures that exhibit a cross machine direction total energy absorption (CDTEA) of greater than 8 cm-g/cm$^2$ as measured by the TEA Test Method and more particularly to fibrous structures that exhibit a CDTEA of greater than 8 cm-g/cm$^2$ as measured according to the TEA Test Method and a Dry Burst of less than 740 g as measured according to the Dry Burst Test Method and a method for making same.

BACKGROUND OF THE INVENTION

Fibrous structures, particularly sanitary tissue products comprising fibrous structures, are known to exhibit different values for particular properties. These differences may translate into one fibrous structure being softer or stronger or more absorbent or more flexible or less flexible or exhibit greater stretch or exhibit less stretch, for example, as compared to another fibrous structure.

One property of fibrous structures that is desirable to consumers is the CDTEA of the fibrous structure. It has been found that at least some consumers desire fibrous structures that exhibit a CDTEA of greater than 8.65 cm-g/cm$^2$ as measured according to the TEA Test Method and/or of greater than 8 cm-g/cm$^2$ as measured according to the TEA Test Method for multi-ply fibrous structures. However, such fibrous structures are not known in the art. Accordingly, there exists a need for fibrous structures that exhibit a CDTEA of greater than 8 cm-g/cm$^2$ as measured according to the TEA Test Method.

SUMMARY OF THE INVENTION

The present invention fulfills the needs described above by providing a fibrous structure that exhibits a CDTEA of greater than 8 cm-g/cm$^2$ as measured according to the TEA Test Method and a method for making same.

In one example of the present invention, a fibrous structure that exhibits a CDTEA of greater than 8.65 cm-g/cm$^2$ as measured according to the TEA Test Method and a Dry Burst of less than 600 g as measured according to the Dry Burst Test Method is provided.

In another example of the present invention, a multi-ply fibrous structure that exhibits a CD TEA of greater than 8 cm-g/cm$^2$ as measured according to the TEA Test Method and a Dry Burst of less than 740 g as measured according to the Dry Burst Test Method is provided.

Accordingly, the present invention provides fibrous structures that exhibit a CDTEA that consumers desire.

DETAILED DESCRIPTION OF THE INVENTION

DEFINITIONS

Figure 1:
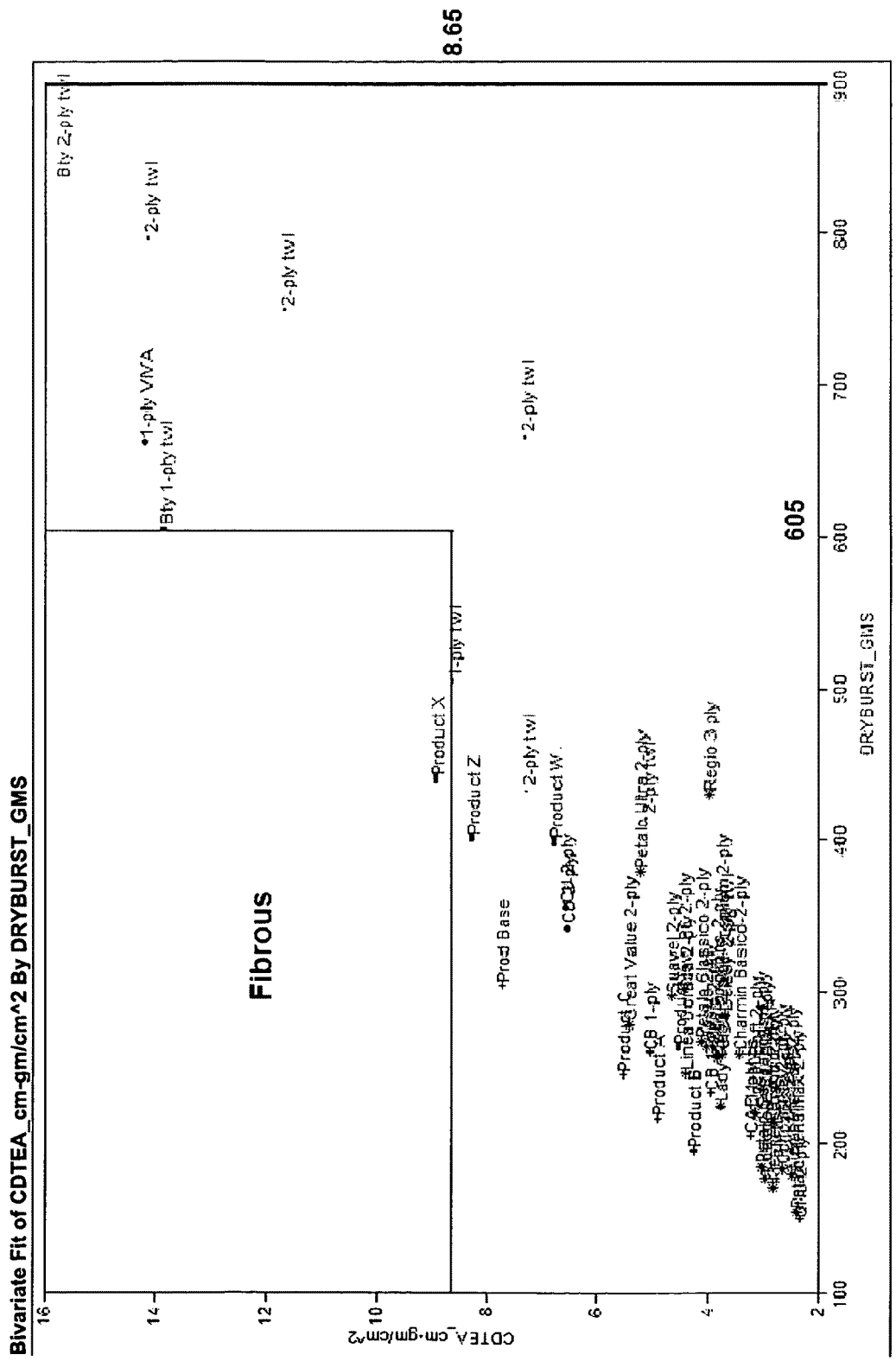
FIG. 1 is a plot of CDTEA to Dry Burst for fibrous structures of the present invention and commercially available fibrous structures, both single-ply and multi-ply sanitary tissue products, illustrating the relatively high level of CDTEA exhibited by the fibrous structures of the present invention.

"Fibrous structure" as used herein means a structure that comprises one or more filaments and/or fibers. In one example, a fibrous structure according to the present invention means an orderly arrangement of filaments and/or fibers within a structure in order to perform a function. Nonlimiting examples of fibrous structures of the present invention include paper, fabrics (including woven, knitted, and nonwoven), and absorbent pads (for example for diapers or feminine hygiene products).

Nonlimiting examples of processes for making fibrous structures include known wet-laid papermaking processes and air-laid papermaking processes. Such processes typically include steps of preparing a fiber composition in the form of a suspension in a medium, either wet, more specifically aqueous medium, or dry, more specifically gaseous, i.e. with air as medium. The aqueous medium used for wet-laid processes is oftentimes referred to as a fiber slurry. The fibrous slurry is then used to deposit a plurality of fibers onto a forming wire or belt such that an embryonic fibrous structure is formed, after which drying and/or bonding the fibers together results in a fibrous structure. Further processing the fibrous structure may be carried out such that a finished fibrous structure is formed. For example, in typical papermaking processes, the finished fibrous structure is the fibrous structure that is wound on the reel at the end of papermaking, and may subsequently be converted into a finished product, e.g. a sanitary tissue product.

The fibrous structures of the present invention may be homogeneous or may be layered. If layered, the fibrous structures may comprise at least two and/or at least three and/or at least four and/or at least five layers.

The fibrous structures of the present invention may be co-formed fibrous structures.

"Co-formed fibrous structure" as used herein means that the fibrous structure comprises a mixture of at least two different materials wherein at least one of the materials comprises a filament, such as a polypropylene filament, and at least one other material, different from the first material, comprises a solid additive, such as a fiber and/or a particulate.

In one example, a co-formed fibrous structure comprises solid additives, such as fibers, such as wood pulp fibers, and filaments, such as polypropylene filaments.

"Solid additive" as used herein means a fiber and/or a particulate.

"Particulate" as used herein means a granular substance or powder.

"Fiber" and/or "Filament" as used herein means an elongate particulate having an apparent length greatly exceeding its apparent width, i.e. a length to diameter ratio of at least about 10. In one example, a "fiber" is an elongate particulate as described above that exhibits a length of less than 5.08 cm (2 in.) and a "filament" is an elongate particulate as described above that exhibits a length of greater than or equal to 5.08 cm (2 in.).

Fibers are typically considered discontinuous in nature. Nonlimiting examples of fibers include wood pulp fibers and synthetic staple fibers such as polyester fibers.

Filaments are typically considered continuous or substantially continuous in nature. Filaments are relatively longer than fibers. Nonlimiting examples of filaments include meltblown and/or spunbond filaments. Nonlimiting examples of materials that can be spun into filaments include natural polymers, such as starch, starch derivatives, cellulose and cellulose derivatives, hemicellulose, hemicellulose derivatives, and synthetic polymers including, but not limited to polyvinyl alcohol filaments and/or polyvinyl alcohol derivative filaments, and thermoplastic polymer filaments, such as polyesters, nylons, polyolefins such as polypropylene filaments, polyethylene filaments, and biodegradable or compostable thermoplastic fibers such as polylactic acid filaments, polyhydroxyalkanoate filaments and polycaprolactone filaments. The filaments may be monocomponent or multicomponent, such as bicomponent filaments.

In one example of the present invention, "fiber" refers to papermaking fibers. Papermaking fibers useful in the present invention include cellulosic fibers commonly known as wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Chemical pulps, however, may be preferred since they impart a superior tactile sense of softness to tissue sheets made therefrom. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified web. U.S. Pat. Nos. 4,300,981 and 3,994,771 are incorporated herein by reference for the purpose of disclosing layering of hardwood and softwood fibers. Also applicable to the present invention are fibers derived from recycled paper, which may contain any or all of the above categories as well as other non-fibrous materials such as fillers and adhesives used to facilitate the original papermaking.

In addition to the various wood pulp fibers, other cellulosic fibers such as cotton linters, rayon, lyocell and bagasse can be used in this invention. Other sources of cellulose in the form of fibers or capable of being spun into fibers include grasses and grain sources.

"Sanitary tissue product" as used herein means a soft, low density (i.e.<about 0.15 g/cm3) web useful as a wiping implement for post-urinary and post-bowel movement cleaning (toilet tissue), for otorhinolaryngological discharges (facial tissue), and multi-functional absorbent and cleaning uses (absorbent towels). The sanitary tissue product may be convolutedly wound upon itself about a core or without a core to form a sanitary tissue product roll.

In one example, the sanitary tissue product of the present invention comprises a fibrous structure according to the present invention.

The sanitary tissue products and/or fibrous structures of the present invention may exhibit a basis weight of greater than 15 g/m2 (9.2 lbs/3000 ft$^2$) to about 120 g/m$^2$ (73.8 lbs/3000 ft$^2$) and/or from about 15 g/m$^2$ (9.2 lbs/3000 ft$^2$) to about 110 g/m$^2$ (67.7 lbs/3000 ft$^2$) and/or from about 20 g/m$^2$ (12.3 lbs/3000 ft$^2$) to about 100 g/m$^2$ (61.5 lbs/3000 ft$^2$) and/or from about 30 (18.5 lbs/3000 ft$^2$) to 90 g/m$^2$ (55.4 lbs/3000 ft$^2$). In addition, the sanitary tissue products and/or fibrous structures of the present invention may exhibit a basis weight between about 40 g/m$^2$ (24.6 lbs/3000 ft$^2$) to about 120 g/m$^2$ (73.8 lbs/3000 ft$^2$) and/or from about 50 g/m$^2$ (30.8 lbs/3000 ft$^2$) to about 110 g/m$^2$ (67.7 lbs/3000 ft$^2$) and/or from about 55 g/m$^2$ (33.8 lbs/3000 ft$^2$) to about 105 g/m$^2$ (64.6 lbs/3000 ft$^2$) and/or from about 60 (36.9 lbs/3000 ft$^2$) to 100 g/m$^2$ (61.5 lbs/3000 ft$^2$).

The sanitary tissue products of the present invention may exhibit a total dry tensile strength of greater than about 59 g/cm (150 g/in) and/or from about 78 g/cm (200 g/in) to about 394 g/cm (1000 g/in) and/or from about 98 g/cm (250 g/in) to about 335 g/cm (850 g/in). In addition, the sanitary tissue product of the present invention may exhibit a total dry tensile strength of greater than about 196 g/cm (500 g/in) and/or from about 196 g/cm (500 g/in) to about 394 g/cm (1000 g/in) and/or from about 216 g/cm (550 g/in) to about 335 g/cm (850 g/in) and/or from about 236 g/cm (600 g/in) to about 315 g/cm (800 g/in). In one example, the sanitary tissue product exhibits a total dry tensile strength of less than about 394 g/cm (1000 g/in) and/or less than about 335 g/cm (850 g/in).

In another example, the sanitary tissue products of the present invention may exhibit a total dry tensile strength of greater than about 196 g/cm (500 g/in) and/or greater than about 236 g/cm (600 g/in) and/or greater than about 276 g/cm (700 g/in) and/or greater than about 315 g/cm (800 g/in) and/or greater than about 354 g/cm (900 g/in) and/or greater than about 394 g/cm (1000 g/in) and/or from about 315 g/cm (800 g/in) to about 1968 g/cm (5000 g/in) and/or from about 354 g/cm (900 g/in) to about 1181 g/cm (3000 g/in) and/or from about 354 g/cm (900 g/in) to about 984 g/cm (2500 g/in) and/or from about 394 g/cm (1000 g/in) to about 787 g/cm (2000 g/in).

The sanitary tissue products of the present invention may exhibit an initial total wet tensile strength of less than about 78 g/cm (200 g/in) and/or less than about 59 g/cm (150 g/in) and/or less than about 39 g/cm (100 g/in) and/or less than about 29 g/cm (75 g/in).

The sanitary tissue products of the present invention may exhibit an initial total wet tensile strength of greater than about 118 g/cm (300 g/in) and/or greater than about 157 g/cm (400 g/in) and/or greater than about 196 g/cm (500 g/in) and/or greater than about 236 g/cm (600 g/in) and/or greater than about 276 g/cm (700 g/in) and/or greater than about 315 g/cm (800 g/in) and/or greater than about 354 g/cm (900 g/in) and/or greater than about 394 g/cm (1000 g/in) and/or from about 118 g/cm (300 g/in) to about 1968 g/cm (5000 g/in) and/or from about 157 g/cm (400 g/in) to about 1181 g/cm (3000 g/in) and/or from about 196 g/cm (500 g/in) to about 984 g/cm (2500 g/in) and/or from about 196 g/cm (500 g/in) to about 787 g/cm (2000 g/in) and/or from about 196 g/cm (500 g/in) to about 591 g/cm (1500 g/in).

The sanitary tissue products of the present invention may exhibit a density (measured at 95 g/in$^2$) of less than about 0.60 g/cm$^3$ and/or less than about 0.30 g/cm$^3$ and/or less than about 0.20 g/cm³ and/or less than about 0.10 g/cm³ and/or less than about 0.07 g/cm³ and/or less than about 0.05 g/cm³ and/or from about 0.01 g/cm³ to about 0.20 g/cm³ and/or from about 0.02 g/cm³ to about 0.10 g/cm³.

The sanitary tissue products of the present invention may exhibit a total absorptive capacity of according to the Horizontal Full Sheet (HFS) Test Method described herein of greater than about 10 g/g and/or greater than about 12 g/g and/or greater than about 15 g/g and/or from about 15 g/g to about 50 g/g and/or to about 40 g/g and/or to about 30 g/g.

The sanitary tissue products of the present invention may exhibit a Vertical Full Sheet (VFS) value as determined by the Vertical Full Sheet (VFS) Test Method described herein of greater than about 5 g/g and/or greater than about 7 g/g and/or greater than about 9 g/g and/or from about 9 g/g to about 30 g/g and/or to about 25 g/g and/or to about 20 g/g and/or to about 17 g/g.

The sanitary tissue products of the present invention may be in the form of sanitary tissue product rolls. Such sanitary tissue product rolls may comprise a plurality of connected, but perforated sheets of fibrous structure, that are separably dispensable from adjacent sheets.

The sanitary tissue products of the present invention may comprises additives such as softening agents, temporary wet strength agents, permanent wet strength agents, bulk softening agents, lotions, silicones, wetting agents, latexes, especially surface-pattern-applied latexes, dry strength agents such as carboxymethylcellulose and starch, and other types of additives suitable for inclusion in and/or on sanitary tissue products.

"Weight average molecular weight" as used herein means the weight average molecular weight as determined using gel permeation chromatography according to the protocol found in Colloids and Surfaces A. Physico Chemical & Engineering Aspects, Vol. 162, 2000, pg. 107-121.

"Basis Weight" as used herein is the weight per unit area of a sample reported in lbs/3000 ft² or g/m² and is measured according to the Basis Weight Test Method described herein.

"Caliper" as used herein means the macroscopic thickness of a fibrous structure. Caliper is measured according to the Caliper Test Method described herein.

"Bulk" as used herein is calculated as the quotient of the Caliper (hereinafter defined), expressed in microns, divided by the basis weight, expressed in grams per square meter. The resulting Bulk is expressed as cubic centimeters per gram. For the products of this invention, Bulks can be greater than about 3 cm³/g and/or greater than about 6 cm³/g and/or greater than about 9 cm³/g and/or greater than about 10.5 cm³/g up to about 30 cm³/g and/or up to about 20 cm³/g. The products of this invention derive the Bulks referred to above from the basesheet, which is the sheet produced by the tissue machine without post treatments such as embossing. Nevertheless, the basesheets of this invention can be embossed to produce even greater bulk or aesthetics, if desired, or they can remain unembossed. In addition, the basesheets of this invention can be calendered to improve smoothness or decrease the Bulk if desired or necessary to meet existing product specifications.

"Basis Weight Ratio" as used herein is the ratio of low basis weight portion of a fibrous structure to a high basis weight portion of a fibrous structure. In one example, the fibrous structures of the present invention exhibit a basis weight ratio of from about 0.02 to about 1. In another example, the basis weight ratio of the basis weight of a linear element of a fibrous structure to another portion of a fibrous structure of the present invention is from about 0.02 to about 1.

"Geometric Mean ("GM") Elongation" as used herein is determined as described in the Elongation Test Method described herein.

"Dry Burst" as used herein is determined as described in the Dry Burst Test Method described herein.

"Geometric Mean ("GM") Modulus" as used herein is determined as described in the Modulus Test Method described herein.

"Machine Direction" or "MD" as used herein means the direction parallel to the flow of the fibrous structure through the fibrous structure making machine and/or sanitary tissue product manufacturing equipment.

"Cross Machine Direction" or "CD" as used herein means the direction parallel to the width of the fibrous structure making machine and/or sanitary tissue product manufacturing equipment and perpendicular to the machine direction.

"Ply" as used herein means an individual, integral fibrous structure.

"Plies" as used herein means two or more individual, integral fibrous structures disposed in a substantially contiguous, face-to-face relationship with one another, forming a multi-ply fibrous structure and/or multi-ply sanitary tissue product. It is also contemplated that an individual, integral fibrous structure can effectively form a multi-ply fibrous structure, for example, by being folded on itself.

"Linear element" as used herein means a discrete, unidirectional, uninterrupted portion of a fibrous structure having length of greater than about 4.5 mm. In one example, a linear element may comprise a plurality of non-linear elements In one example, a linear element in accordance with the present invention is water-resistant. Unless otherwise stated, the linear elements of the present invention are present on a surface of a fibrous structure. The length and/or width and/or height of the linear element and/or linear element forming component within a molding member, which results in a linear element within a fibrous structure, is measured by the Dimensions of Linear Element/Linear Element Forming Component Test Method described herein.

In one example, the linear element and/or linear element forming component is continuous or substantially continuous with a useable fibrous structure, for example in one case one or more 11 cm×11 cm sheets of fibrous structure.

"Discrete" as it refers to a linear element means that a linear element has at least one immediate adjacent region of the fibrous structure that is different from the linear element.

"Unidirectional" as it refers to a linear element means that along the length of the linear element, the linear element does not exhibit a directional vector that contradicts the linear element's major directional vector.

"Uninterrupted" as it refers to a linear element means that a linear element does not have a region that is different from the linear element cutting across the linear element along its length. Undulations within a linear element such as those resulting from operations such creping and/or foreshortening are not considered to result in regions that are different from the linear element and thus do not interrupt the linear element along its length.

"Water-resistant" as it refers to a linear element means that a linear element retains its structure and/or integrity after being saturated.

"Substantially machine direction oriented" as it refers to a linear element means that the total length of the linear element that is positioned at an angle of greater than 45° to the cros machine direction is greater than the total length of the linear element that is positioned at an angle of 45° or less to the cross machine direction.

"Substantially cross machine direction oriented" as it refers to a linear element means that the total length of the linear element that is positioned at an angle of 45° or greater to the machine direction is greater than the total length of the linear element that is positioned at an angle of less than 45° to the machine direction.

Fibrous Structure

The fibrous structures of the present invention may be a single-ply or multi-ply fibrous structure.

In one example of the present invention as shown in FIG. 1, a fibrous structure, for example a multi-ply fibrous structure, exhibits a CDTEA of greater than 8 cm-g/cm$^2$ and/or greater than about 8.2 cm-g/cm$^2$ and/or greater than about 8.5 cm-g/cm$^2$ and/or greater than about 8.7 cm-g/cm$^2$ as measured according to the TEA Test Method. In another example of the present invention as shown in FIG. 1, a fibrous structure, for example a single-ply fibrous structure, exhibits a CDTEA of greater than 8.7 cm-g/cm$^2$ and/or greater than about 8.8 cm-g/cm$^2$ and/or greater than about 8.9 cm-g/cm$^2$ as measured according to the TEA Test Method.

In another example of the present invention as shown in FIG. 1, a fibrous structure exhibits a Dry Burst of less than 600 g and/or from about 100 g to about 600 g and/or from about 370 g to about 500 g as measured according to the Dry Burst Test Method. In even another example of the present invention as shown in FIG. 1, a fibrous structure, such as a multi-ply fibrous structure exhibits a Dry Burst of less than 740 g and/or from about 100 g to about 740 g and/or from about 370 g to about 740 g and/or from about 370 g to about 600 g and/or from about 370 g to about 500 g as measured according to the Dry Burst Test Method.

Table 1 below shows the physical property values of fibrous structures in accordance with the present invention and commercially available fibrous structures.

| Fibrous Structure | # of Plies | CDTEA cm-g/cm$^2$ | Dry Burst g | Basis Weight gsm |
|---|---|---|---|---|
| Invention | 2 | 15.9 | 399 | 38.3 |
| Invention | 2 | 17.5 | 439 | 39.1 |
| Charmin ® Basic | 1 | 17.4 | 215 | 29.4 |
| Charmin ® Basic | 1 | 17.2 | 194 | 28.8 |
| Charmin ® Ultra Strong | 2 | 14.9 | 303 | 38.1 |
| Cottonelle ® Ultra | 2 | 15.5 | 356 | 44.5 |
| Cottonelle ® Ultra | 2 | 13.9 | 341 | 42.8 |
| Cottonelle ® with Ripples | 1 | 15.7 | 259 | 30.5 |
| Bounty ® Basic | 1 | 16.9 | 605 | 43.7 |
| Kleenex Viva ® | 1 | 23 | 663 | 65.5 |
| Quilted Northern ® Ultra | 2 | 14.1 | 148 | 45.7 |
| Quilted Northern ® | 1 | 13 | 218 | 37.5 |
| Angel Soft ® | 2 | 11.8 | 217 | 34.3 |

In even yet another example of the present invention, a fibrous structure comprises cellulosic pulp fibers. However, other naturally-occurring and/or non-naturally occurring fibers and/or filaments may be present in the fibrous structures of the present invention.

In one example of the present invention, a fibrous structure comprises a throughdried fibrous structure. The fibrous structure may be creped or uncreped. In one example, the fibrous structure is a wet-laid fibrous structure.

The fibrous structure may be incorporated into a single- or multi-ply sanitary tissue product. The sanitary tissue product may be in roll form where it is convolutedly wrapped about itself with or without the employment of a core.

Figure 2:
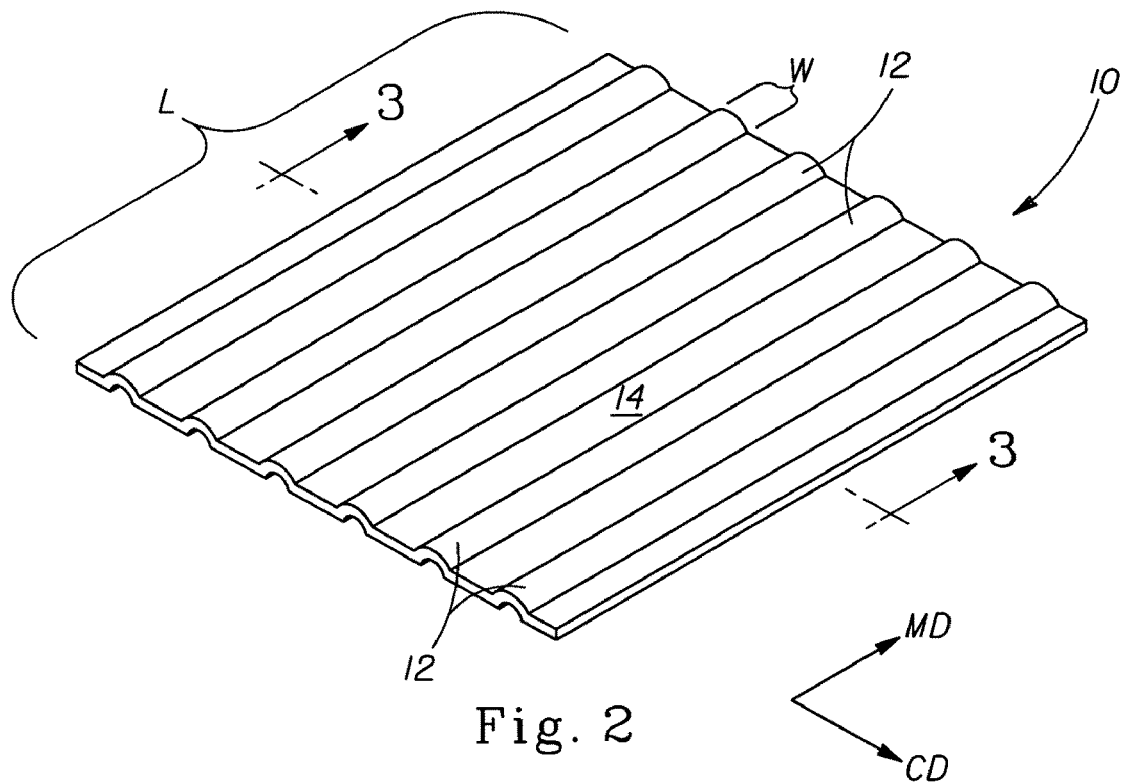
FIG. 2 is a schematic representation of an example of a fibrous structure in accordance with the present invention.
Figure 3:
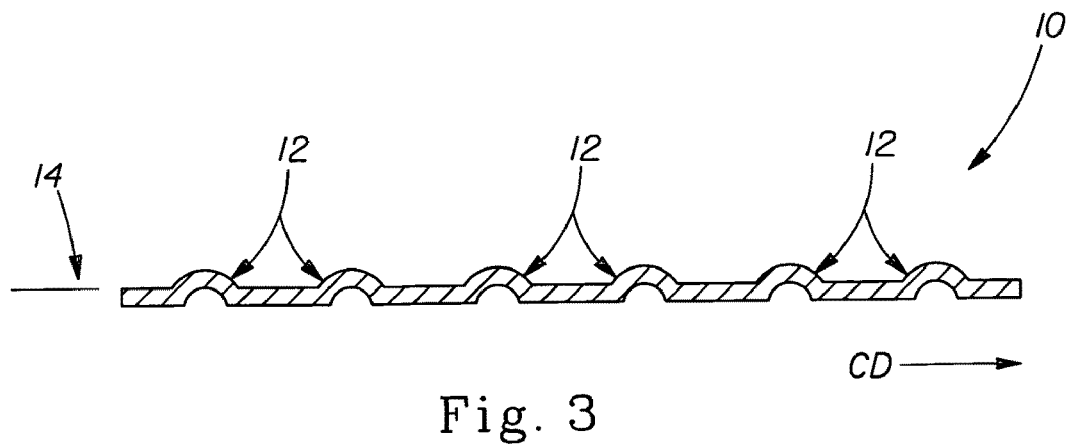
FIG. 3 is a cross-sectional view of FIG. 2 taken along line 3-3.
Figure 4:
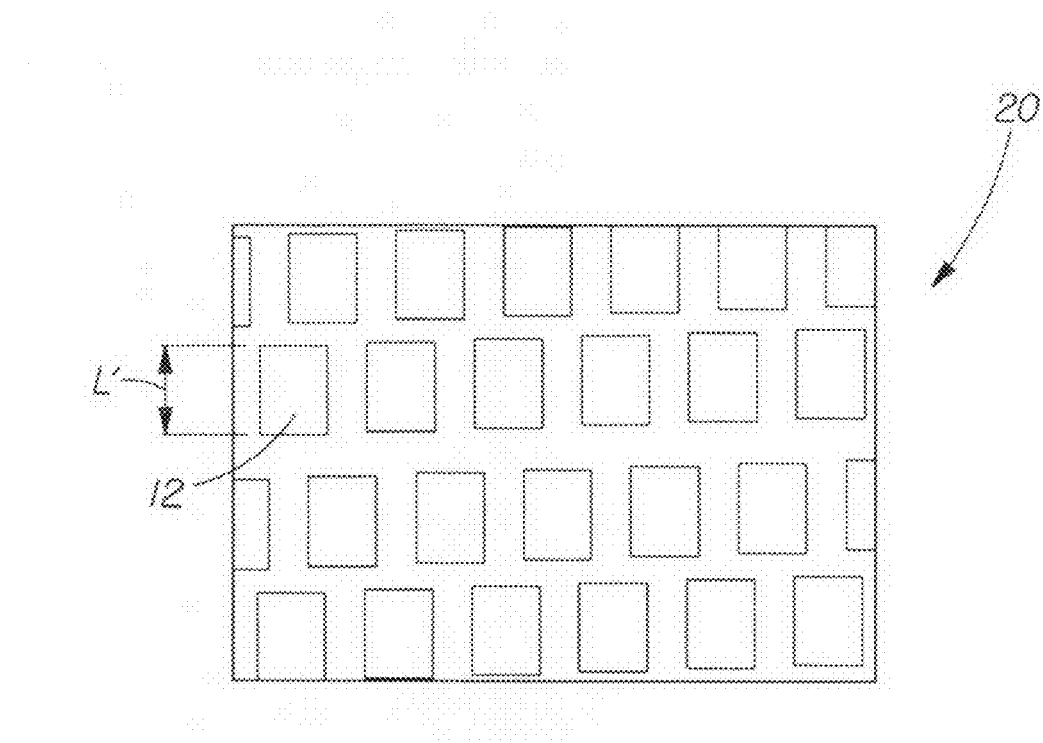
FIG. 4 is a schematic representation of a prior art fibrous structure comprising linear elements.
Figure 5:
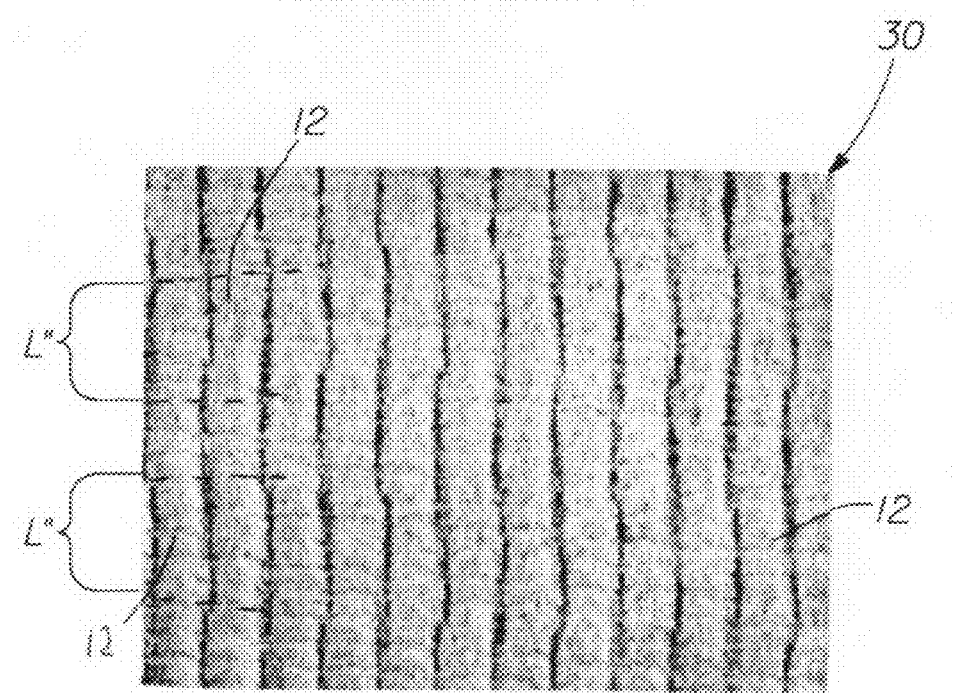
FIG. 5 is an electromicrograph of a portion of a prior art fibrous structure.

A nonlimiting example of a fibrous structure in accordance with the present invention is shown in FIGS. 2 and 3. FIGS. 2 and 3 show a fibrous structure 10 comprising one or more linear elements 12. The linear elements 12 are oriented in the machine or substantially the machine direction on the surface 14 of the fibrous structure 10. In one example, one or more of the linear elements 12 may exhibit a length L of greater than about 4.5 mm and/or greater than about 6 mm and/or greater than about 10 mm and/or greater than about 20 mm and/or greater than about 30 mm and/or greater than about 45 mm and/or greater than about 60 mm and/or greater than about 75 mm and/or greater than about 90 mm. For comparison, as shown in FIG. 4, a schematic representation of a commercially available toilet tissue product 20 has a plurality of substantially machine direction oriented linear elements 12 wherein the longest linear element 12 present in the toilet tissue product 20 exhibits a length L' of 4.3 mm or less. FIG. 5 is a micrograph of a surface of a commercially available toilet tissue product 30 that comprises substantially machine direction oriented linear elements 12 wherein the longest linear element 12 present in the toilet tissue product 30 exhibits a length L" of 4.3 mm or less.

In one example, the width W of one or more of the linear elements 12 is less than about 10 mm and/or less than about 7 mm and/or less than about 5 mm and/or less than about 2 mm and/or less than about 1.7 mm and/or less than about 1.5 mm to about 0 mm and/or to about 0.10 mm and/or to about 0.20 mm. In another example, the linear element height of one or more of the linear elements is greater than about 0.10 mm and/or greater than about 0.50 mm and/or greater than about 0.75 mm and/or greater than about 1 mm to about 4 mm and/or to about 3 mm and/or to about 2.5 mm and/or to about 2 mm.

In another example, the fibrous structure of the present invention exhibits a ratio of linear element height (in mm) to linear element width (in mm) of greater than about 0.35 and/or greater than about 0.45 and/or greater than about 0.5 and/or greater than about 0.75 and/or greater than about 1.

One or more of the linear elements may exhibit a geometric mean of linear element height by linear element of width of greater than about 0.25 mm$^2$ and/or greater than about 0.35 mm$^2$ and/or greater than about 0.5 mm$^2$ and/or greater than about 0.75 mm$^2$.

As shown in FIGS. 2 and 3, the fibrous structure 10 may comprise a plurality of substantially machine direction oriented linear elements 12 that are present on the fibrous structure 10 at a frequency of greater than about 1 linear element/5 cm and/or greater than about 4 linear elements/5 cm and/or greater than about 7 linear elements/5 cm and/or greater than about 15 linear elements/5 cm and/or greater than about 20 linear elements/5 cm and/or greater than about 25 linear elements/5 cm and/or greater than about 30 linear elements/5 cm up to about 50 linear elements/5 cm and/or to about 40 linear elements/5 cm.

In another example of a fibrous structure according to the present invention, the fibrous structure exhibits a ratio of a frequency of linear elements (per cm) to the width (in cm) of one linear element of greater than about 3 and/or greater than about 5 and/or greater than about 7.

The linear elements of the present invention may be in any shape, such as lines, zig-zag lines, serpentine lines. In one example, a linear element does not intersect another linear element.

Figure 6:
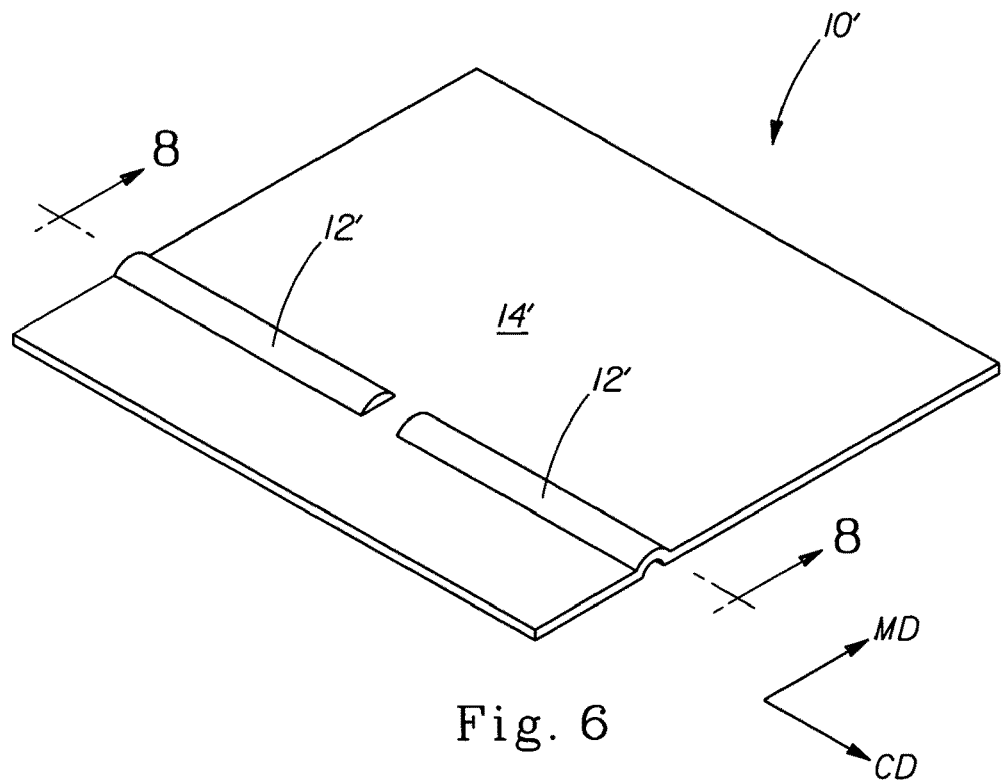
FIG. 6 is a schematic representation of an example of a fibrous structure according to the present invention.
Figure 7:
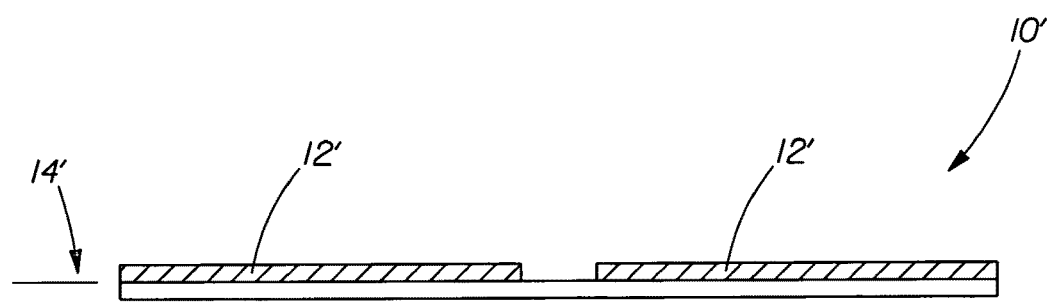
FIG. 7 is a cross-section view of FIG. 6 taken along line 7-7.

As shown in FIGS. 6 and 7, a fibrous structure 10' of the present invention may comprise one or more linear elements 12'. The linear elements 12' may be oriented on a surface 14' of a fibrous structure 12' in any direction such as machine direction, cross machine direction, substantially machine direction oriented, substantially cross machine direction oriented. Two or more linear elements may be oriented in different directions on the same surface of a fibrous structure according to the present invention. In the case of FIGS. 6 and 7, the linear elements 12' are oriented in the cross machine direction. Even though the fibrous structure 10' comprises only two linear elements 12', it is within the scope of the present invention for the fibrous structure 10' to comprise three or more linear elements 12'.

The dimensions (length, width and/or height) of the linear elements of the present invention may vary from linear element to linear element within a fibrous structure. As a result, the gap width between neighboring linear elements may vary from one gap to another within a fibrous structure.

In one example, the linear element may comprise an embossment. In another example, the linear element may be an embossed linear element rather than a linear element formed during a fibrous structure making process.

In another example, a plurality of linear elements may be present on a surface of a fibrous structure in a pattern such as in a corduroy pattern.

In still another example, a surface of a fibrous structure may comprise a discontinuous pattern of a plurality of linear elements wherein at least one of the linear elements exhibits a linear element length of greater than about 30 mm.

In yet another example, a surface of a fibrous structure comprises at least one linear element that exhibits a width of less than about 10 mm and/or less than about 7 mm and/or less than about 5 mm and/or less than about 3 mm and/or to about 0.01 mm and/or to about 0.1 mm and/or to about 0.5 mm.

The linear elements may exhibit any suitable height known to those of skill in the art. For example, a linear element may exhibit a height of greater than about 0.10 mm and/or greater than about 0.20 mm and/or greater than about 0.30 mm to about 3.60 mm and/or to about 2.75 mm and/or to about 1.50 mm. A linear element's height is measured irrespective of arrangement of a fibrous structure in a multi-ply fibrous structure, for example, the linear element's height may extend inward within the fibrous structure.

The fibrous structures of the present invention may comprise at least one linear element that exhibits a height to width ratio of greater than about 0.350 and/or greater than about 0.450 and/or greater than about 0.500 and/or greater than about 0.600 and/or to about 3 and/or to about 2 and/or to about 1.

In another example, a linear element on a surface of a fibrous structure may exhibit a geometric mean of height by width of greater than about 0.250 and/or greater than about 0.350 and/or greater than about 0.450 and/or to about 3 and/or to about 2 and/or to about 1.

The fibrous structures of the present invention may comprise linear elements in any suitable frequency. For example, a surface of a fibrous structure may comprises linear elements at a frequency of greater than about 1 linear element/5 cm and/or greater than about 1 linear element/3 cm and/or greater than about 1 linear element/cm and/or greater than about 3 linear elements/cm.

In one example, a fibrous structure comprises a plurality of linear elements that are present on a surface of the fibrous structure at a ratio of frequency of linear elements to width of at least one linear element of greater than about 3 and/or greater than about 5 and/or greater than about 7.

The fibrous structure of the present invention may comprise a surface comprising a plurality of linear elements such that the ratio of geometric mean of height by width of at least one linear element to frequency of linear elements is greater than about 0.050 and/or greater than about 0.750 and/or greater than about 0.900 and/or greater than about 1 and/or greater than about 2 and/or up to about 20 and/or up to about 15 and/or up to about 10.

Figure 8:
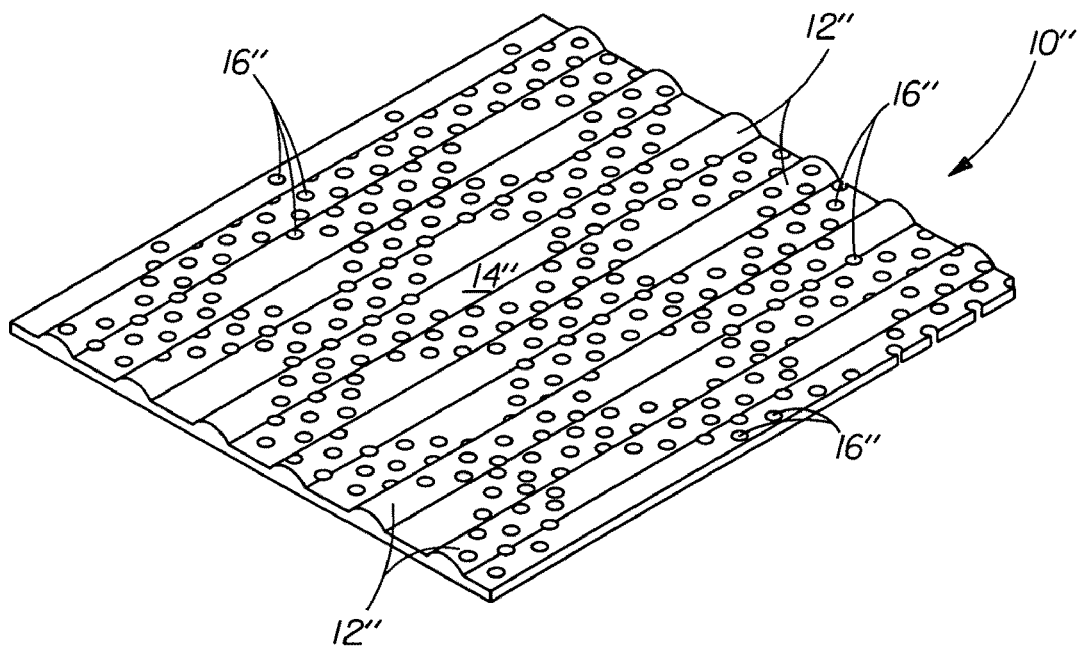
FIG. 8 is a schematic representation of an example of a fibrous structure according to the present invention.

In addition to one or more linear elements 12", as shown in FIG. 8, a fibrous structure 10" of the present invention may further comprise one or more non-linear elements 16". In one example, a non-linear element 16" present on the surface 14" of a fibrous structure 10" is water-resistant. In another example, a non-linear element 16" present on the surface 14" of a fibrous structure 10" comprises an embossment. When present on a surface of a fibrous structure, a plurality of non-linear elements may be present in a pattern. The pattern may comprise a geometric shape such as a polygon. Nonlimiting example of suitable polygons are selected from the group consisting of: triangles, diamonds, trapezoids, parallelograms, rhombuses, stars, pentagons, hexagons, octagons and mixtures thereof.

Figure 9:
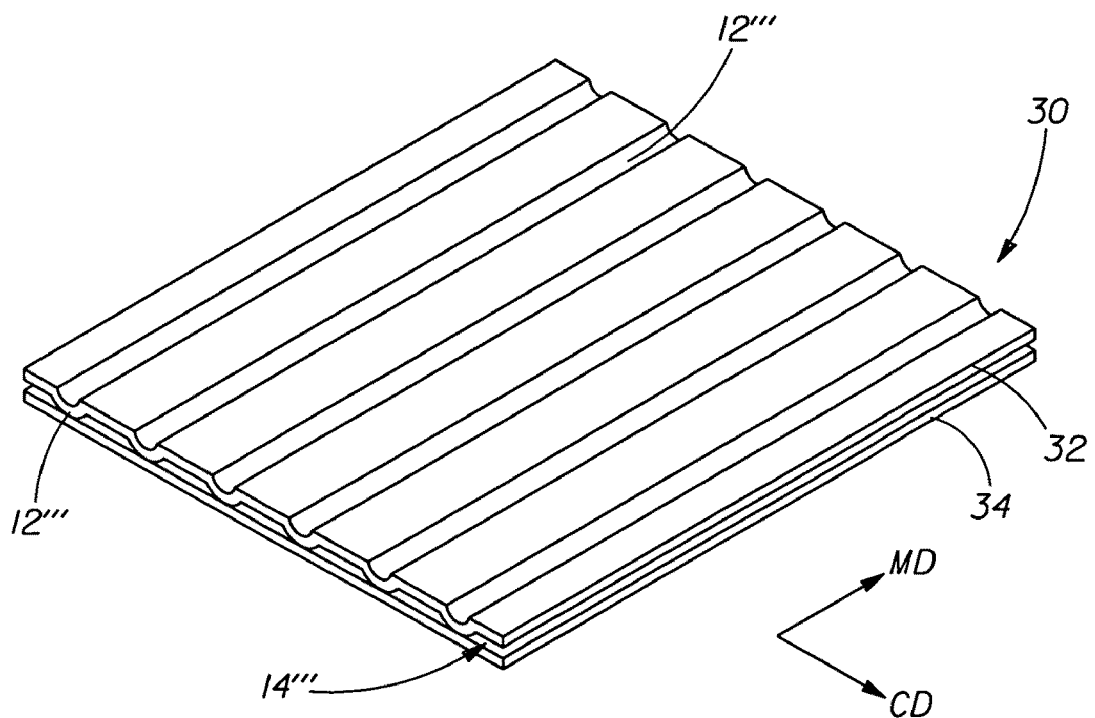
FIG. 9 is a schematic representation of an example of a fibrous structure according to the present invention.

One or more of the fibrous structures of the present invention may form a single- or multi-ply sanitary tissue product. In one example, as shown in FIG. 9, a multi-ply sanitary tissue product 30 comprises a first ply 32 and a second ply 34 wherein the first ply 32 comprises a surface 14''' comprising a plurality of linear elements 12''', in this case being oriented in the machine direction or substantially machine direction oriented. The plies 32 and 34 are arranged such that the linear elements 12''' extend inward into the interior of the sanitary tissue product 30 rather than outward.

Figure 10:
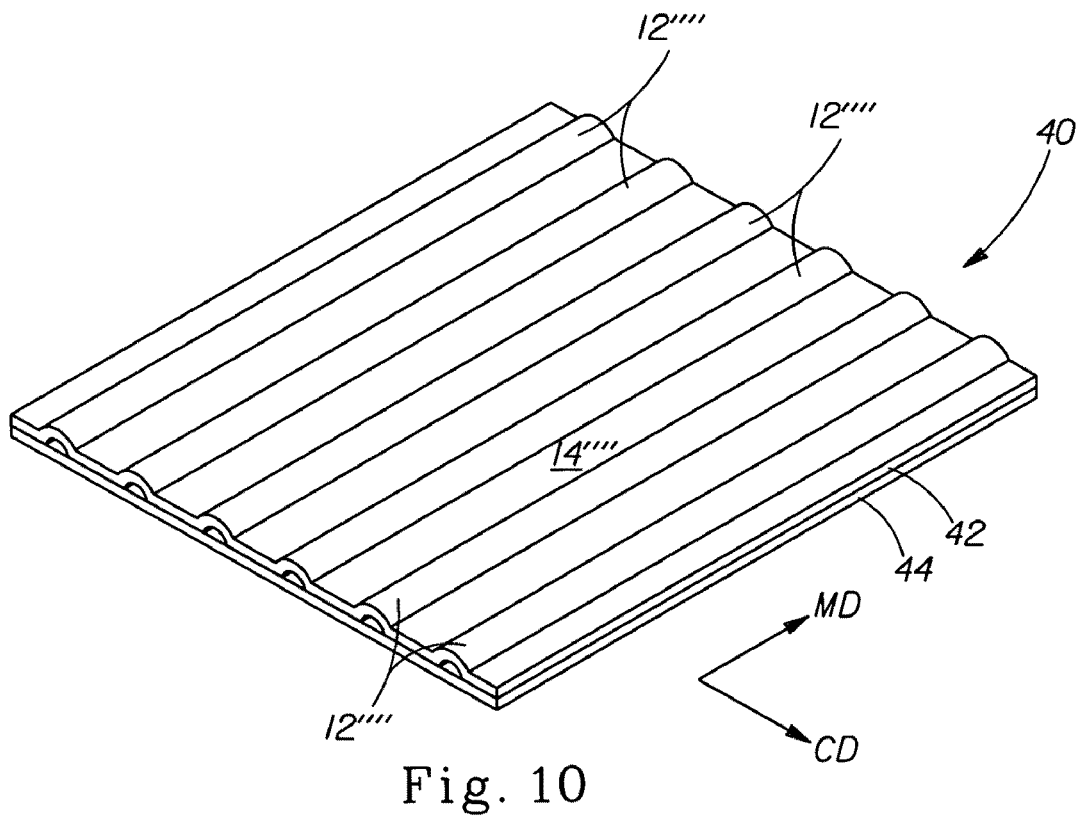
FIG. 10 is a schematic representation of an example of a fibrous structure according to the present invention.

In another example, as shown in FIG. 10, a multi-ply sanitary tissue product 40 comprises a first ply 42 and a second ply 44 wherein the first ply 42 comprises a surface 14'''' comprising a plurality of linear elements 12'''', in this case being oriented in the machine direction or substantially machine direction oriented. The plies 42 and 44 are arranged such that the linear elements 12'''' extend outward from the surface 14'''' of the sanitary tissue product 40 rather than inward into the interior of the sanitary tissue product 40.

Figure 11:
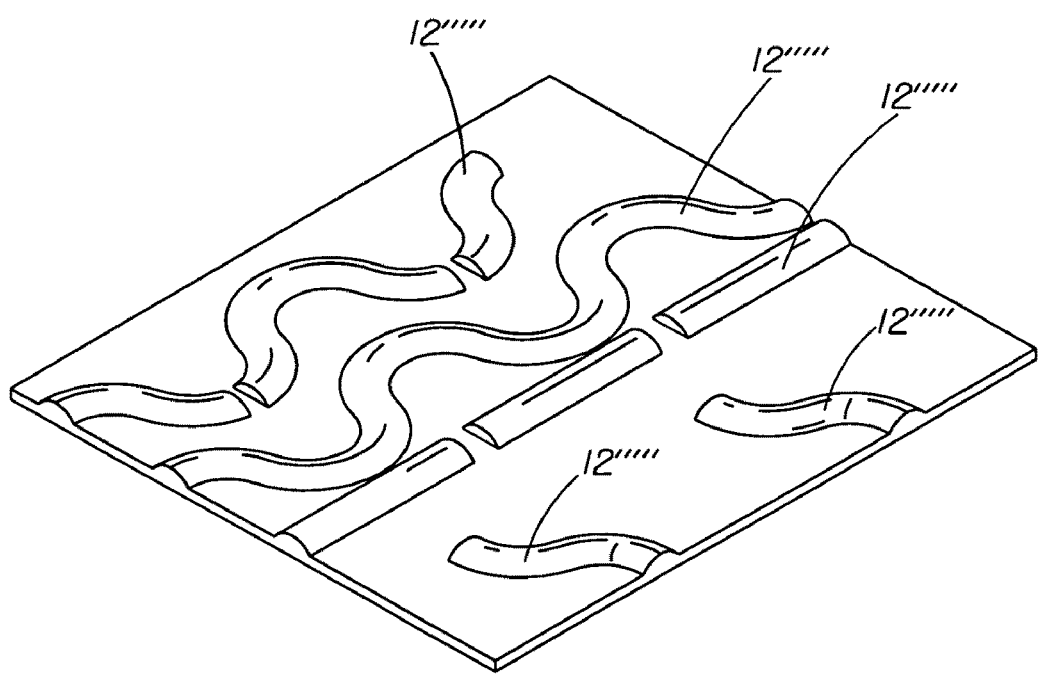
FIG. 11 is a schematic representation of an example of a fibrous structure comprising various forms of linear elements in accordance with the present invention.

As shown in FIG. 11, a fibrous structure 10''' of the present invention may comprise a variety of different forms of linear elements 12''''', alone or in combination, such as serpentines, dashes, MD and/or CD oriented, and the like.

Methods for Making Fibrous Structures

The fibrous structures of the present invention may be made by any suitable process known in the art. The method may be a fibrous structure making process that uses a cylindrical dryer such as a Yankee (a Yankee-process) or it may be a Yankeeless process as is used to make substantially uniform density and/or uncreped fibrous structures.

The fibrous structure of the present invention may be made using a molding member. A "molding member" is a structural element that can be used as a support for an embryonic web comprising a plurality of cellulosic fibers and a plurality of synthetic fibers, as well as a forming unit to form, or "mold," a desired microscopical geometry of the fibrous structure of the present invention. The molding member may comprise any element that has fluid-permeable areas and the ability to impart a microscopical three-dimensional pattern to the structure being produced thereon, and includes, without limitation, single-layer and multi-layer structures comprising a stationary plate, a belt, a woven fabric (including Jacquard-type and the like woven patterns), a band, and a roll. In one example, the molding member is a deflection member.

A "reinforcing element" is a desirable (but not necessary) element in some embodiments of the molding member, serving primarily to provide or facilitate integrity, stability, and durability of the molding member comprising, for example, a resinous material. The reinforcing element can be fluid-permeable or partially fluid-permeable, may have a variety of embodiments and weave patterns, and may comprise a variety of materials, such as, for example, a plurality of interwoven yarns (including Jacquard-type and the like woven patterns), a felt, a plastic, other suitable synthetic material, or any combination thereof.

In one example of a method for making a fibrous structure of the present invention, the method comprises the step of contacting an embryonic fibrous web with a deflection member (molding member) such that at least one portion of the embryonic fibrous web is deflected out-of-plane of another portion of the embryonic fibrous web. The phrase "out-of-plane" as used herein means that the fibrous structure comprises a protuberance, such as a dome, or a cavity that extends away from the plane of the fibrous structure. The molding member may comprise a through-air-drying fabric having its filaments arranged to produce linear elements within the fibrous structures of the present invention and/or the through-air-drying fabric or equivalent may comprise a resinous framework that defines deflection conduits that allow portions of the fibrous structure to deflect into the conduits thus forming linear elements within the fibrous structures of the present invention. In addition, a forming wire, such as a foraminous member may be arranged such that linear elements within the fibrous structures of the present invention are formed and/or like the through-air-drying fabric, the foraminous member may comprise a resinous framework that defines deflection conduits that allow portions of the fibrous structure to deflect into the conduits thus forming linear elements within the fibrous structures of the present invention.

In another example of a method for making a fibrous structure of the present invention, the method comprises the steps of:

(a) providing a fibrous furnish comprising fibers; and
(b) depositing the fibrous furnish onto a deflection member such that at least one fiber is deflected out-of-plane of the other fibers present on the deflection member.

In still another example of a method for making a fibrous structure of the present invention, the method comprises the steps of:

(a) providing a fibrous furnish comprising fibers;
(b) depositing the fibrous furnish onto a foraminous member to form an embryonic fibrous web;
(c) associating the embryonic fibrous web with a deflection member such that at least one fiber is deflected out-of-plane of the other fibers present in the embryonic fibrous web; and
(d) drying said embryonic fibrous web such that that the dried fibrous structure is formed.

In another example of a method for making a fibrous structure of the present invention, the method comprises the steps of:

(a) providing a fibrous furnish comprising fibers;
(b) depositing the fibrous furnish onto a first foraminous member such that an embryonic fibrous web is formed;
(c) associating the embryonic web with a second foraminous member which has one surface (the embryonic fibrous web-contacting surface) comprising a macroscopically monoplanar network surface which is continuous and patterned and which defines a first region of deflection conduits and a second region of deflection conduits within the first region of deflection conduits;

(d) deflecting the fibers in the embryonic fibrous web into the deflection conduits and removing water from the embryonic web through the deflection conduits so as to form an intermediate fibrous web under such conditions that the deflection of fibers is initiated no later than the time at which the water removal through the deflection conduits is initiated; and (e) optionally, drying the intermediate fibrous web; and (f) optionally, foreshortening the intermediate fibrous web.

The fibrous structures of the present invention may be made by a method wherein a fibrous furnish is applied to a first foraminous member to produce an embryonic fibrous web. The embryonic fibrous web may then come into contact with a second foraminous member that comprises a deflection member to produce an intermediate fibrous web that comprises a network surface and at least one dome region. The intermediate fibrous web may then be further dried to form a fibrous structure of the present invention.

Figure 12:
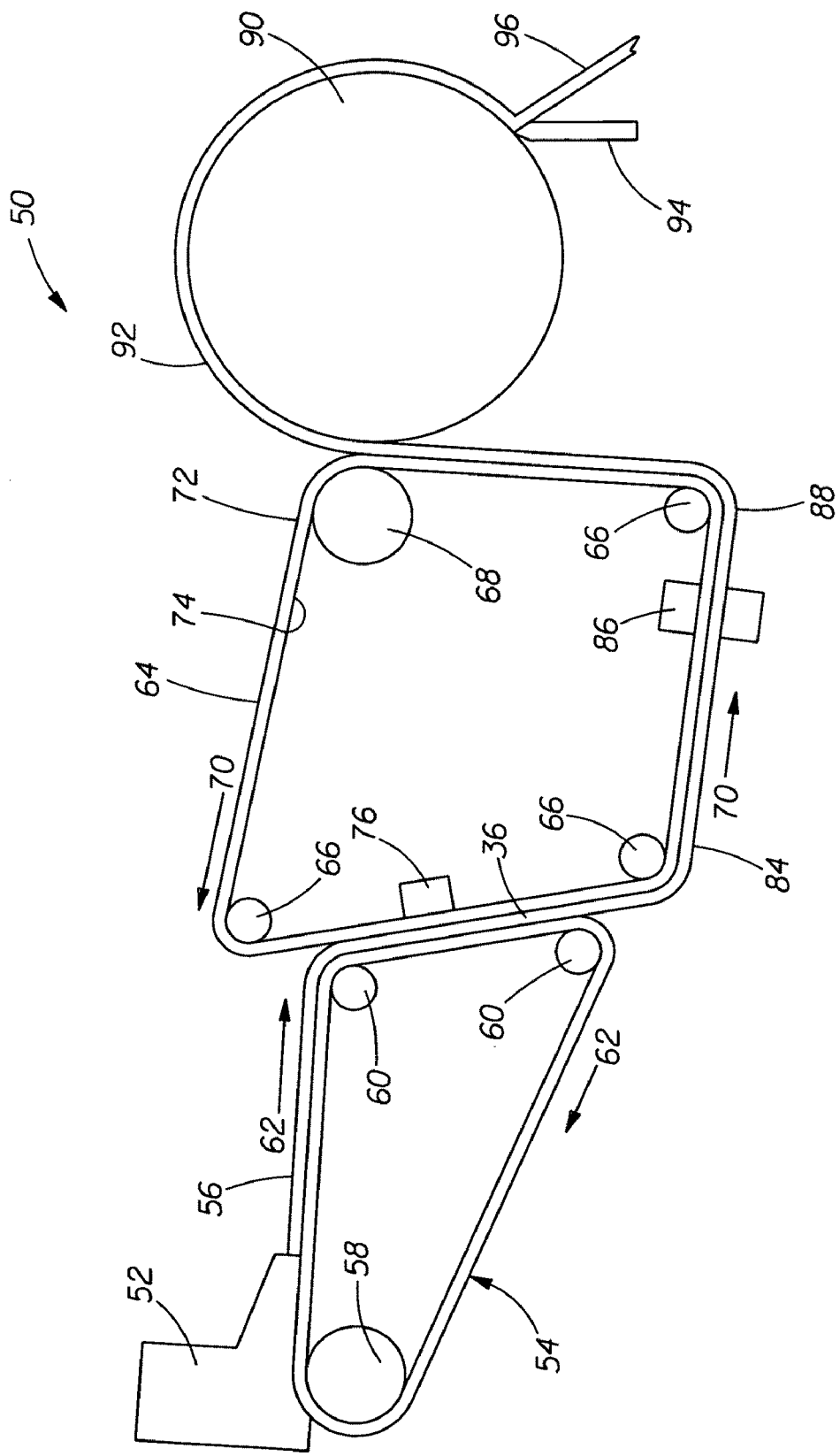
FIG. 12 is a schematic representation of an example of a method for making a fibrous structure according to the present invention.

FIG. 12 is a simplified, schematic representation of one example of a continuous fibrous structure making process and machine useful in the practice of the present invention.

As shown in FIG. 12, one example of a process and equipment, represented as 50 for making a fibrous structure according to the present invention comprises supplying an aqueous dispersion of fibers (a fibrous furnish) to a headbox 52 which can be of any convenient design. From headbox 52 the aqueous dispersion of fibers is delivered to a first foraminous member 54 which is typically a Fourdrinier wire, to produce an embryonic fibrous web 56.

The first foraminous member 54 may be supported by a breast roll 58 and a plurality of return rolls 60 of which only two are shown. The first foraminous member 54 can be propelled in the direction indicated by directional arrow 62 by a drive means, not shown. Optional auxiliary units and/or devices commonly associated fibrous structure making machines and with the first foraminous member 54, but not shown, include forming boards, hydrofoils, vacuum boxes, tension rolls, support rolls, wire cleaning showers, and the like.

After the aqueous dispersion of fibers is deposited onto the first foraminous member 54, embryonic fibrous web 56 is formed, typically by the removal of a portion of the aqueous dispersing medium by techniques well known to those skilled in the art. Vacuum boxes, forming boards, hydrofoils, and the like are useful in effecting water removal. The embryonic fibrous web 56 may travel with the first foraminous member 54 about return roll 60 and is brought into contact with a deflection member 64, which may also be referred to as a second foraminous member. While in contact with the deflection member 64, the embryonic fibrous web 56 will be deflected, rearranged, and/or further dewatered.

The deflection member 64 may be in the form of an endless belt. In this simplified representation, deflection member 64 passes around and about deflection member return rolls 66 and impression nip roll 68 and may travel in the direction indicated by directional arrow 70. Associated with deflection member 64, but not shown, may be various support rolls, other return rolls, cleaning means, drive means, and the like well known to those skilled in the art that may be commonly used in fibrous structure making machines.

Regardless of the physical form which the deflection member 64 takes, whether it is an endless belt as just discussed or some other embodiment such as a stationary plate for use in making handsheets or a rotating drum for use with other types of continuous processes, it must have certain physical characteristics. For example, the deflection member may take a variety of configurations such as belts, drums, flat plates, and the like.

First, the deflection member 64 may be foraminous. That is to say, it may possess continuous passages connecting its first surface 72 (or "upper surface" or "working surface"; i.e. the surface with which the embryonic fibrous web is associated, sometimes referred to as the "embryonic fibrous web-contacting surface") with its second surface 74 (or "lower surface"; i.e., the surface with which the deflection member return rolls are associated). In other words, the deflection member 64 may be constructed in such a manner that when water is caused to be removed from the embryonic fibrous web 56, as by the application of differential fluid pressure, such as by a vacuum box 76, and when the water is removed from the embryonic fibrous web 56 in the direction of the deflection member 64, the water can be discharged from the system without having to again contact the embryonic fibrous web 56 in either the liquid or the vapor state.

Figure 13:
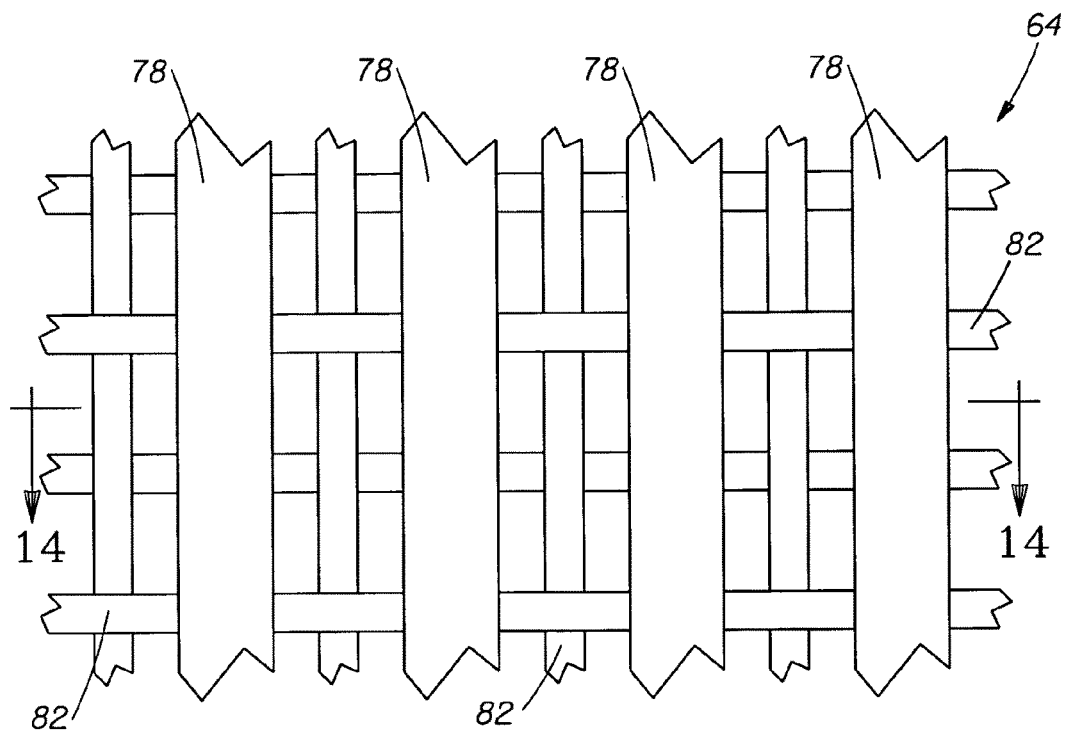
FIG. 13 is a schematic representation a portion of an example of a molding member in according with the present invention.
Figure 14:
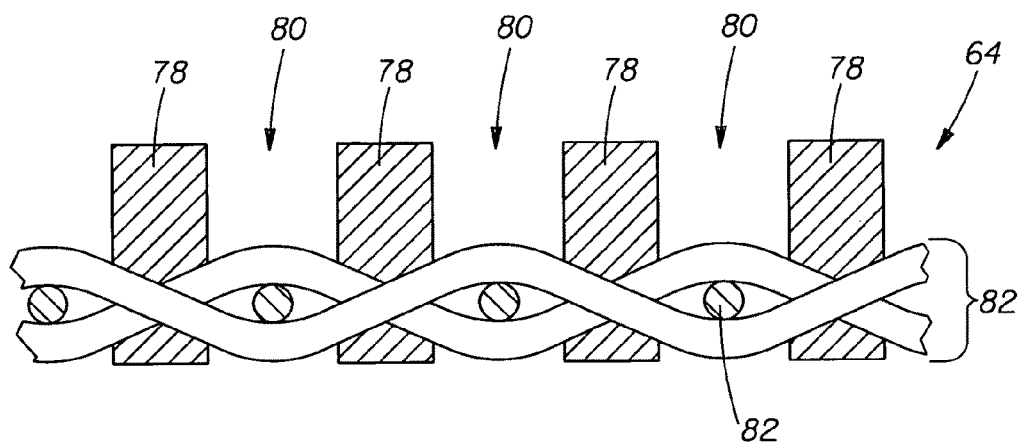
FIG. 14 is a cross-section view of FIG. 13 taken along line 14-14.

Second, the first surface 72 of the deflection member 64 may comprise one or more ridges 78 as represented in one example in FIGS. 13 and 14. The ridges 78 may be made by any suitable material. For example, a resin may be used to create the ridges 78. The ridges 78 may be continuous, or essentially continuous. In one example, the ridges 78 exhibit a length of greater than about 30 mm. The ridges 78 may be arranged to produce the fibrous structures of the present invention when utilized in a suitable fibrous structure making process. The ridges 78 may be patterned. The ridges 78 may be present on the deflection member 64 at any suitable frequency to produce the fibrous structures of the present invention. The ridges 78 may define within the deflection member 64 a plurality of deflection conduits 80. The deflection conduits 80 may be discrete, isolated, deflection conduits.

The deflection conduits 80 of the deflection member 64 may be of any size and shape or configuration so long at least one produces a linear element in the fibrous structure produced thereby. The deflection conduits 80 may repeat in a random pattern or in a uniform pattern. Portions of the deflection member 64 may comprise deflection conduits 80 that repeat in a random pattern and other portions of the deflection member 64 may comprise deflection conduits 80 that repeat in a uniform pattern.

The ridges 78 of the deflection member 64 may be associated with a belt, wire or other type of substrate. As shown in FIGS. 13 and 14, the ridges 78 of the deflection member 64 is associated with a woven belt 82. The woven belt 82 may be made by any suitable material, for example polyester, known to those skilled in the art.

As shown in FIG. 14, a cross sectional view of a portion of the deflection member 64 taken along line 14-14 of FIG. 13, the deflection member 64 can be foraminous since the deflection conduits 80 extend completely through the deflection member 64.

In one example, the deflection member of the present invention may be an endless belt which can be constructed by, among other methods, a method adapted from techniques used to make stencil screens. By "adapted" it is meant that the broad, overall techniques of making stencil screens are used, but improvements, refinements, and modifications as discussed below are used to make member having significantly greater thickness than the usual stencil screen.

Broadly, a foraminous member (such as a woven belt) is thoroughly coated with a liquid photosensitive polymeric resin to a preselected thickness. A mask or negative incorporating the pattern of the preselected ridges is juxtaposed the liquid photosensitive resin; the resin is then exposed to light of an appropriate wave length through the mask. This exposure to light causes curing of the resin in the exposed areas. Unexpected (and uncured) resin is removed from the system leaving behind the cured resin forming the ridges defining within it a plurality of deflection conduits.

In another example, the deflection member can be prepared using as the foraminous member, such as a woven belt, of width and length suitable for use on the chosen fibrous structure making machine. The ridges and the deflection conduits are formed on this woven belt in a series of sections of convenient dimensions in a batchwise manner, i.e. one section at a time. Details of this nonlimiting example of a process for preparing the deflection member follow.

First, a planar forming table is supplied. This forming table is at least as wide as the width of the foraminous woven element and is of any convenient length. It is provided with means for securing a backing film smoothly and tightly to its surface. Suitable means include provision for the application of vacuum through the surface of the forming table, such as a plurality of closely spaced orifices and tensioning means.

A relatively thin, flexible polymeric (such as polypropylene) backing film is placed on the forming table and is secured thereto, as by the application of vacuum or the use of tension. The backing film serves to protect the surface of the forming table and to provide a smooth surface from which the cured photosensitive resins will, later, be readily released. This backing film will form no part of the completed deflection member.

Either the backing film is of a color which absorbs activating light or the backing film is at least semi-transparent and the surface of the forming table absorbs activating light.

A thin film of adhesive, such as 8091 Crown Spray Heavy Duty Adhesive made by Crown Industrial Products Co. of Hebron, Ill., is applied to the exposed surface of the backing film or, alternatively, to the knuckles of the woven belt. A section of the woven belt is then placed in contact with the backing film where it is held in place by the adhesive. The woven belt is under tension at the time it is adhered to the backing film.

Next, the woven belt is coated with liquid photosensitive resin. As used herein, "coated" means that the liquid photosensitive resin is applied to the woven belt where it is carefully worked and manipulated to insure that all the openings (interstices) in the woven belt are filled with resin and that all of the filaments comprising the woven belt are enclosed with the resin as completely as possible. Since the knuckles of the woven belt are in contact with the backing film, it will not be possible to completely encase the whole of each filament with photosensitive resin. Sufficient additional liquid photosensitive resin is applied to the woven belt to form a deflection member having a certain preselected thickness. The deflection member can be from about 0.35 mm (0.014 in.) to about 3.0 mm (0.150 in.) in overall thickness and the ridges can be spaced from about 0.10 mm (0.004 in.) to about 2.54 mm (0.100 in.) from the mean upper surface of the knuckles of the woven belt. Any technique well known to those skilled in the art can be used to control the thickness of the liquid photosensitive resin coating. For example, shims of the appropriate thickness can be provided on either side of the section of deflection member under construction; an excess quantity of liquid photosensitive resin can be applied to the woven belt between the shims; a straight edge resting on the shims and can then be drawn across the surface of the liquid photosensitive resin thereby removing excess material and forming a coating of a uniform thickness.

Suitable photosensitive resins can be readily selected from the many available commercially. They are typically materials, usually polymers, which cure or cross-link under the influence of activating radiation, usually ultraviolet (UV) light. References containing more information about liquid photosensitive resins include Green et al, "Photocross-linkable Resin Systems," J. Macro. Sci-Revs. Macro. Chem, C21 (2), 187-273 (1981-82); Boyer, "A Review of Ultraviolet Curing Technology," Tappi Paper Synthetics Conf. Proc., Sep. 25-27, 1978, pp 167-172; and Schmidle, "Ultraviolet Curable Flexible Coatings," J. of Coated Fabrics, 8, 10-20 (July, 1978). All the preceding three references are incorporated herein by reference. In one example, the ridges are made from the Merigraph series of resins made by Hercules Incorporated of Wilmington, Del.

Once the proper quantity (and thickness) of liquid photosensitive resin is coated on the woven belt, a cover film is optionally applied to the exposed surface of the resin. The cover film, which must be transparent to light of activating wave length, serves primarily to protect the mask from direct contact with the resin.

A mask (or negative) is placed directly on the optional cover film or on the surface of the resin. This mask is formed of any suitable material which can be used to shield or shade certain portions of the liquid photosensitive resin from light while allowing the light to reach other portions of the resin. The design or geometry preselected for the ridges is, of course, reproduced in this mask in regions which allow the transmission of light while the geometries preselected for the gross foramina are in regions which are opaque to light.

A rigid member such as a glass cover plate is placed atop the mask and serves to aid in maintaining the upper surface of the photosensitive liquid resin in a planar configuration.

The liquid photosensitive resin is then exposed to light of the appropriate wave length through the cover glass, the mask, and the cover film in such a manner as to initiate the curing of the liquid photosensitive resin in the exposed areas. It is important to note that when the described procedure is followed, resin which would normally be in a shadow cast by a filament, which is usually opaque to activating light, is cured. Curing this particular small mass of resin aids in making the bottom side of the deflection member planar and in isolating one deflection conduit from another.

After exposure, the cover plate, the mask, and the cover film are removed from the system. The resin is sufficiently cured in the exposed areas to allow the woven belt along with the resin to be stripped from the backing film.

Uncured resin is removed from the woven belt by any convenient means such as vacuum removal and aqueous washing.

A section of the deflection member is now essentially in final form. Depending upon the nature of the photosensitive resin and the nature and amount of the radiation previously supplied to it, the remaining, at least partially cured, photosensitive resin can be subjected to further radiation in a post curing operation as required.

The backing film is stripped from the forming table and the process is repeated with another section of the woven belt. Conveniently, the woven belt is divided off into sections of essentially equal and convenient lengths which are numbered serially along its length. Odd numbered sections are sequentially processed to form sections of the deflection member and then even numbered sections are sequentially processed until the entire belt possesses the characteristics required of the deflection member. The woven belt may be maintained under tension at all times.

In the method of construction just described, the knuckles of the woven belt actually form a portion of the bottom surface of the deflection member. The woven belt can be physically spaced from the bottom surface.

Multiple replications of the above described technique can be used to construct deflection members having the more complex geometries.

The deflection member of the present invention may be made or partially made according to U.S. Pat. No. 4,637,859, issued Jan. 20, 1987 to Trokhan.

As shown in FIG. 12, after the embryonic fibrous web 56 has been associated with the deflection member 64, fibers within the embryonic fibrous web 56 are deflected into the deflection conduits present in the deflection member 64. In one example of this process step, there is essentially no water removal from the embryonic fibrous web 56 through the deflection conduits after the embryonic fibrous web 56 has been associated with the deflection member 64 but prior to the deflecting of the fibers into the deflection conduits. Further water removal from the embryonic fibrous web 56 can occur during and/or after the time the fibers are being deflected into the deflection conduits. Water removal from the embryonic fibrous web 56 may continue until the consistency of the embryonic fibrous web 56 associated with deflection member 64 is increased to from about 25% to about 35%. Once this consistency of the embryonic fibrous web 56 is achieved, then the embryonic fibrous web 56 is referred to as an intermediate fibrous web 84. During the process of forming the embryonic fibrous web 56, sufficient water may be removed, such as by a noncompressive process, from the embryonic fibrous web 56 before it becomes associated with the deflection member 64 so that the consistency of the embryonic fibrous web 56 may be from about 10% to about 30%.

While applicants decline to be bound by any particular theory of operation, it appears that the deflection of the fibers in the embryonic web and water removal from the embryonic web begin essentially simultaneously. Embodiments can, however, be envisioned wherein deflection and water removal are sequential operations. Under the influence of the applied differential fluid pressure, for example, the fibers may be deflected into the deflection conduit with an attendant rearrangement of the fibers. Water removal may occur with a continued rearrangement of fibers. Deflection of the fibers, and of the embryonic fibrous web, may cause an apparent increase in surface area of the embryonic fibrous web. Further, the rearrangement of fibers may appear to cause a rearrangement in the spaces or capillaries existing between and/or among fibers.

It is believed that the rearrangement of the fibers can take one of two modes dependent on a number of factors such as, for example, fiber length. The free ends of longer fibers can be merely bent in the space defined by the deflection conduit while the opposite ends are restrained in the region of the ridges. Shorter fibers, on the other hand, can actually be transported from the region of the ridges into the deflection conduit (The fibers in the deflection conduits will also be rearranged relative to one another). Naturally, it is possible for both modes of rearrangement to occur simultaneously.

As noted, water removal occurs both during and after deflection; this water removal may result in a decrease in fiber mobility in the embryonic fibrous web. This decrease in fiber mobility may tend to fix and/or freeze the fibers in place after they have been deflected and rearranged. Of course, the drying of the web in a later step in the process of this invention serves to more firmly fix and/or freeze the fibers in position.

Any convenient means conventionally known in the papermaking art can be used to dry the intermediate fibrous web 84. Examples of such suitable drying process include subjecting the intermediate fibrous web 84 to conventional and/or flow-through dryers and/or Yankee dryers.

In one example of a drying process, the intermediate fibrous web 84 in association with the deflection member 64 passes around the deflection member return roll 66 and travels in the direction indicated by directional arrow 70. The intermediate fibrous web 84 may first pass through an optional predryer 86. This predryer 86 can be a conventional flow-through dryer (hot air dryer) well known to those skilled in the art. Optionally, the predryer 86 can be a so-called capillary dewatering apparatus. In such an apparatus, the intermediate fibrous web 84 passes over a sector of a cylinder having preferential-capillary-size pores through its cylindrical-shaped porous cover. Optionally, the predryer 86 can be a combination capillary dewatering apparatus and flow-through dryer. The quantity of water removed in the predryer 86 may be controlled so that a predried fibrous web 88 exiting the predryer 86 has a consistency of from about 30% to about 98%. The predried fibrous web 88, which may still be associated with deflection member 64, may pass around another deflection member return roll 66 and as it travels to an impression nip roll 68. As the predried fibrous web 88 passes through the nip formed between impression nip roll 68 and a surface of a Yankee dryer 90, the ridge pattern formed by the top surface 72 of deflection member 64 is impressed into the predried fibrous web 88 to form a linear element imprinted fibrous web 92. The imprinted fibrous web 92 can then be adhered to the surface of the Yankee dryer 90 where it can be dried to a consistency of at least about 95%.

The imprinted fibrous web 92 can then be foreshortened by creping the imprinted fibrous web 92 with a creping blade 94 to remove the imprinted fibrous web 92 from the surface of the Yankee dryer 90 resulting in the production of a creped fibrous structure 96 in accordance with the present invention. As used herein, foreshortening refers to the reduction in length of a dry (having a consistency of at least about 90% and/or at least about 95%) fibrous web which occurs when energy is applied to the dry fibrous web in such a way that the length of the fibrous web is reduced and the fibers in the fibrous web are rearranged with an accompanying disruption of fiber-fiber bonds. Foreshortening can be accomplished in any of several well-known ways. One common method of foreshortening is creping. The creped fibrous structure 96 may be subjected to post processing steps such as calendaring, tuft generating operations, and/or embossing and/or converting.

In addition to the Yankee fibrous structure making process/method, the fibrous structures of the present invention may be made using a Yankeeless fibrous structure making process/method. Such a process oftentimes utilizes transfer fabrics to permit rush transfer of the embryonic fibrous web prior to drying. The fibrous structures produced by such a Yankeeless fibrous structure making process oftentimes a substantially uniform density.

The molding member/deflection member of the present invention may be utilized to imprint linear elements into a fibrous structure during a through-air-drying operation.

However, such molding members/deflection members may also be utilized as forming members upon which a fiber slurry is deposited.

In one example, the linear elements of the present invention may be formed by a plurality of non-linear element, such as embossments and/or protrusions and/or depressions formed by a molding member, that are arranged in a line having an overall length of greater than about 4.5 mm and/or greater than about 10 mm and/or greater than about 15 mm and/or greater than about 25 mm and/or greater than about 30 mm.

In addition to imprinting linear elements into fibrous structures during a fibrous structure making process/method, linear elements may be created in a fibrous structure during a converting operation of a fibrous structure. For example, linear elements may be imparted to a fibrous structure by embossing linear elements into a fibrous structure.

Nonlimiting Example

A fibrous structure in accordance with the present invention is prepared using a fibrous structure making machine having a layered headbox having a top chamber, a center chamber, and a bottom chamber. A eucalyptus fiber slurry is pumped through the top headbox chamber, a eucalyptus fiber slurry is pumped through the bottom headbox chamber (i.e. the chamber feeding directly onto the forming wire) and, finally, an NSK fiber slurry is pumped through the center headbox chamber and delivered in superposed relation onto the Fourdrinier wire to form thereon a three-layer embryonic web, of which about 33% of the top side is made up of the eucalyptus blended fibers, 33% is made of the eucalyptus fibers on the bottom side and 33% is made up of the NSK fibers in the center. Dewatering occurs through the Fourdrinier wire and is assisted by a deflector and vacuum boxes. The Fourdrinier wire is of a 5-shed, satin weave configuration having 87 machine-direction and 76 cross-machine-direction monofilaments per inch, respectively. The speed of the Fourdrinier wire is about 750 fpm (feet per minute).

The embryonic wet web is transferred from the Fourdrinier wire, at a fiber consistency of about 15% at the point of transfer, to a patterned drying fabric. The speed of the patterned drying fabric is the same as the speed of the Fourdrinier wire. The drying fabric is designed to yield a pattern of substantially machine direction oriented linear channels having a continuous network of high density (knuckle) areas. This drying fabric is formed by casting an impervious resin surface onto a fiber mesh supporting fabric. The supporting fabric is a 45×52 filament, dual layer mesh. The thickness of the resin cast is about 11 mils above the supporting fabric.

Further de-watering is accomplished by vacuum assisted drainage until the web has a fiber consistency of about 20% to 30%.

While remaining in contact with the patterned drying fabric, the web is pre-dried by air blow-through pre-dryers to a fiber consistency of about 65% by weight.

After the pre-dryers, the semi-dry web is transferred to the Yankee dryer and adhered to the surface of the Yankee dryer with a sprayed creping adhesive. The creping adhesive is an aqueous dispersion with the actives consisting of about 22% polyvinyl alcohol, about 11% CREPETROL A3025, and about 67% CREPETROL R6390. CREPETROL A3025 and CREPETROL R6390 are commercially available from Hercules Incorporated of Wilmington, Del. The creping adhesive is delivered to the Yankee surface at a rate of about 0.15% adhesive solids based on the dry weight of the web. The fiber consistency is increased to about 97% before the web is dry creped from the Yankee with a doctor blade.

The doctor blade has a bevel angle of about 25 degrees and is positioned with respect to the Yankee dryer to provide an impact angle of about 81 degrees. The Yankee dryer is operated at a temperature of about 350° F. (177° C.) and a speed of about 750 fpm. The fibrous structure is wound in a roll using a surface driven reel drum having a surface speed of about 656 feet per minute. The fibrous structure may be subjected to post treatments such as embossing and/or tuft generating. The fibrous structure may be subsequently converted into a two-ply sanitary tissue product having a basis weight of about 39 g/m². For each ply, the outer layer having the eucalyptus fiber furnish is oriented toward the outside in order to form the consumer facing surfaces of the two-ply sanitary tissue product.

The sanitary tissue product is soft, flexible and absorbent.

Test Methods

Unless otherwise specified, all tests described herein including those described under the Definitions section and the following test methods are conducted on samples that have been conditioned in a conditioned room at a temperature of 73° F.±4° F. (about 23° C.±2.2° C.) and a relative humidity of 50%±10% for 2 hours prior to the test. All plastic and paper board packaging materials must be carefully removed from the paper samples prior to testing. Discard any damaged product. All tests are conducted in such conditioned room.

Basis Weight Test Method

Basis weight of a fibrous structure sample is measured by selecting twelve (12) usable units (also referred to as sheets) of the fibrous structure and making two stacks of six (6) usable units each. Perforation must be aligned on the same side when stacking the usable units. A precision cutter is used to cut each stack into exactly 8.89 cm×8.89 cm (3.5 in.×3.5 in.) squares. The two stacks of cut squares are combined to make a basis weight pad of twelve (12) squares thick. The basis weight pad is then weighed on a top loading balance with a minimum resolution of 0.01 g. The top loading balance must be protected from air drafts and other disturbances using a draft shield. Weights are recorded when the readings on the top loading balance become constant. The Basis Weight is calculated as follows:

$$\text{Basis Weight(lbs/3000 ft}^2) = \frac{\text{Weight of basis weight pad(g)} \times 3000 \text{ ft}^2}{453.6 \text{ g/lbs} \times 12(\text{usable units}) \times [12.25 \text{ in}^2(\text{Area of basis weight pad})/144 \text{ in}^2]}$$

$$\text{Basis Weight(g/m}^2) = \frac{\text{Weight of basis weight pad(g)} \times 10,000 \text{ cm}^2/\text{m}^2}{79.0321 \text{ cm}^2(\text{Are of basis weight pad}) \times 12(\text{usable units})}$$

Caliper Test Method

Caliper of a fibrous structure is measured by cutting five (5) samples of fibrous structure such that each cut sample is larger in size than a load foot loading surface of a VIR Electronic Thickness Tester Model II available from Thwing-Albert Instrument Company, Philadelphia, Pa. Typically, the load foot loading surface has a circular surface area of about 3.14 in². The sample is confined between a horizontal flat surface and the load foot loading surface. The load foot loading surface applies a confining pressure to the sample of 15.5 g/cm². The caliper of each sample is the resulting gap between the flat surface and the load foot loading surface. The caliper is calculated as the average caliper of the five samples. The result is reported in millimeters (mm).

Elongation, Tensile Strength, TEA and Modulus Test Methods

Remove five (5) strips of four (4) usable units (also referred to as sheets) of fibrous structures and stack one on top of the other to form a long stack with the perforations between the sheets coincident. Identify sheets 1 and 3 for machine direction tensile measurements and sheets 2 and 4 for cross direction tensile measurements. Next, cut through the perforation line using a paper cutter (JDC-1-10 or JDC-1-12 with safety shield from Thwing-Albert Instrument Co. of Philadelphia, Pa.) to make 4 separate stacks. Make sure stacks 1 and 3 are still identified for machine direction testing and stacks 2 and 4 are identified for cross direction testing.

Cut two 1 inch (2.54 cm) wide strips in the machine direction from stacks 1 and 3. Cut two 1 inch (2.54 cm) wide strips in the cross direction from stacks 2 and 4. There are now four 1 inch (2.54 cm) wide strips for machine direction tensile testing and four 1 inch (2.54 cm) wide strips for cross direction tensile testing. For these finished product samples, all eight 1 inch (2.54 cm) wide strips are five usable units (sheets) thick.

For the actual measurement of the elongation, tensile strength, TEA and modulus, use a Thwing-Albert Intelect II Standard Tensile Tester (Thwing-Albert Instrument Co. of Philadelphia, Pa.). Insert the flat face clamps into the unit and calibrate the tester according to the instructions given in the operation manual of the Thwing-Albert Intelect II. Set the instrument crosshead speed to 4.00 in/min (10.16 cm/min) and the 1st and 2nd gauge lengths to 2.00 inches (5.08 cm). The break sensitivity is set to 20.0 grams and the sample width is set to 1.00 inch (2.54 cm) and the sample thickness is set to 0.3937 inch (1 cm). The energy units are set to TEA and the tangent modulus (Modulus) trap setting is set to 38.1 g.

Take one of the fibrous structure sample strips and place one end of it in one clamp of the tensile tester. Place the other end of the fibrous structure sample strip in the other clamp. Make sure the long dimension of the fibrous structure sample strip is running parallel to the sides of the tensile tester. Also make sure the fibrous structure sample strips are not overhanging to the either side of the two clamps. In addition, the pressure of each of the clamps must be in full contact with the fibrous structure sample strip.

After inserting the fibrous structure sample strip into the two clamps, the instrument tension can be monitored. If it shows a value of 5 grams or more, the fibrous structure sample strip is too taut. Conversely, if a period of 2-3 seconds passes after starting the test before any value is recorded, the fibrous structure sample strip is too slack.

Start the tensile tester as described in the tensile tester instrument manual. The test is complete after the crosshead automatically returns to its initial starting position. When the test is complete, read and record the following with units of measure:

Peak Load Tensile (Tensile Strength) (g/in)
Peak Elongation (Elongation) (%)
Peak TEA (TEA) (in-g/in²)
Tangent Modulus (Modulus) (at 15 g/cm)

Test each of the samples in the same manner, recording the above measured values from each test.

Calculations:
Geometric Mean (GM) Elongation=Square Root of [MD Elongation (%)×CD Elongation (%)]
Total Dry Tensile (TDT)=Peak Load MD Tensile (g/in)+Peak Load CD Tensile (g/in)
Tensile Ratio=Peak Load MD Tensile (g/in)/Peak Load CD Tensile (g/in)
Geometric Mean (GM) Tensile=[Square Root of (Peak Load MD Tensile (g/in)×Peak Load CD Tensile (g/in))]×3
TEA=MD TEA (in-g/in²)+CD TEA (in-g/in²)
Geometric Mean (GM) TEA=Square Root of [MD TEA (in-g/in²)×CD TEA (in-g/in²)]
Modulus=MD Modulus (15 g/cm)+CD Modulus (15 g/cm)

Geometric Mean (GM) Modulus=Square Root of [MD Modulus (15 g/cm)×CD Modulus (15 g/cm)]

Dry Burst Test Method

Fibrous structure samples for each condition to be tested are cut to a size appropriate for testing (minimum sample size 4.5 inches×4.5 inches), a minimum of five (5) samples for each condition to be tested are prepared.

A burst tester (Burst Tester Intelect-II-STD Tensile Test Instrument, Cat. No. 1451-24PGB available from Thwing-Albert Instrument Co., Philadelphia, Pa.) is set up according to the manufacturer's instructions and the following conditions: Speed: 12.7 centimeters per minute; Break Sensitivity: 20 grams; and Peak Load: 2000 grams. The load cell is calibrated according to the expected burst strength.

A fibrous structure sample to be tested is clamped and held between the annular clamps of the burst tester and is subjected to increasing force that is applied by a 0.625 inch diameter, polished stainless steel ball upon operation of the burst tester according to the manufacturer's instructions. The burst strength is that force that causes the sample to fail.

The burst strength for each fibrous structure sample is recorded. An average and a standard deviation for the burst strength for each condition is calculated.

The Dry Burst is reported as the average and standard deviation for each condition to the nearest gram.

Horizontal Full Sheet (HFS) Test Method

The Horizontal Full Sheet (HFS) test method determines the amount of distilled water absorbed and retained by a fibrous structure of the present invention. This method is performed by first weighing a sample of the fibrous structure to be tested (referred to herein as the "dry weight of the sample"), then thoroughly wetting the sample, draining the wetted sample in a horizontal position and then reweighing (referred to herein as "wet weight of the sample"). The absorptive capacity of the sample is then computed as the amount of water retained in units of grams of water absorbed by the sample. When evaluating different fibrous structure samples, the same size of fibrous structure is used for all samples tested.

The apparatus for determining the HFS capacity of fibrous structures comprises the following:

1) An electronic balance with a sensitivity of at least ±0.01 grams and a minimum capacity of 1200 grams. The balance should be positioned on a balance table and slab to minimize the vibration effects of floor/benchtop weighing. The balance should also have a special balance pan to be able to handle the size of the sample tested (i.e.; a fibrous structure sample of about 11 in. (27.9 cm) by 11 in. (27.9 cm)). The balance pan can be made out of a variety of materials. Plexiglass is a common material used.

2) A sample support rack (FIG. 16) and sample support rack cover (FIG. 17) is also required. Both the rack and cover are comprised of a lightweight metal frame, strung with 0.012 in. (0.305 cm) diameter monofilament so as to form a grid as shown in FIG. 16. The size of the support rack and cover is such that the sample size can be conveniently placed between the two.

The HFS test is performed in an environment maintained at 23±1° C. and 50±2% relative humidity. A water reservoir or tub is filled with distilled water at 23±1° C. to a depth of 3 inches (7.6 cm).

Eight samples of a fibrous structure to be tested are carefully weighed on the balance to the nearest 0.01 grams. The dry weight of each sample is reported to the nearest 0.01 grams. The empty sample support rack is placed on the balance with the special balance pan described above. The balance is then zeroed (tared). One sample is carefully placed on the sample support rack. The support rack cover is placed on top of the support rack. The sample (now sandwiched between the rack and cover) is submerged in the water reservoir. After the sample is submerged for 60 seconds, the sample support rack and cover are gently raised out of the reservoir.

The sample, support rack and cover are allowed to drain horizontally for 120±5 seconds, taking care not to excessively shake or vibrate the sample. While the sample is draining, the rack cover is carefully removed and all excess water is wiped from the support rack. The wet sample and the support rack are weighed on the previously tared balance. The weight is recorded to the nearest 0.01 g. This is the wet weight of the sample.

The gram per fibrous structure sample absorptive capacity of the sample is defined as (wet weight of the sample−dry weight of the sample). The horizontal absorbent capacity (HAC) is defined as: absorbent capacity=(wet weight of the sample−dry weight of the sample)/(dry weight of the sample) and has a unit of gram/gram.

Vertical Full Sheet (VFS) Test Method

The Vertical Full Sheet (VFS) test method determines the amount of distilled water absorbed and retained by a fibrous structure of the present invention. This method is performed by first weighing a sample of the fibrous structure to be tested (referred to herein as the "dry weight of the sample"), then thoroughly wetting the sample, draining the wetted sample in a vertical position and then reweighing (referred to herein as "wet weight of the sample"). The absorptive capacity of the sample is then computed as the amount of water retained in units of grams of water absorbed by the sample. When evaluating different fibrous structure samples, the same size of fibrous structure is used for all samples tested.

The apparatus for determining the VFS capacity of fibrous structures comprises the following:

1) An electronic balance with a sensitivity of at least ±0.01 grams and a minimum capacity of 1200 grams. The balance should be positioned on a balance table and slab to minimize the vibration effects of floor/benchtop weighing. The balance should also have a special balance pan to be able to handle the size of the sample tested (i.e.; a fibrous structure sample of about 11 in. (27.9 cm) by 11 in. (27.9 cm)). The balance pan can be made out of a variety of materials. Plexiglass is a common material used.

2) A sample support rack (FIG. 16) and sample support rack cover (FIG. 17) is also required. Both the rack and cover are comprised of a lightweight metal frame, strung with 0.012 in. (0.305 cm) diameter monofilament so as to form a grid as shown in FIG. 16. The size of the support rack and cover is such that the sample size can be conveniently placed between the two.

The VFS test is performed in an environment maintained at 23±1° C. and 50±2% relative humidity. A water reservoir or tub is filled with distilled water at 23±1° C. to a depth of 3 inches (7.6 cm).

Eight 19.05 cm (7.5 inch)×19.05 cm (7.5 inch) to 27.94 cm (11 inch)×27.94 cm (11 inch) samples of a fibrous structure to be tested are carefully weighed on the balance to the nearest 0.01 grams. The dry weight of each sample is reported to the nearest 0.01 grams. The empty sample support rack is placed on the balance with the special balance pan described above. The balance is then zeroed (tared). One sample is carefully placed on the sample support rack. The support rack cover is placed on top of the support rack. The sample (now sandwiched between the rack and cover) is submerged in the water reservoir. After the sample is submerged for 60 seconds, the sample support rack and cover are gently raised out of the reservoir.

The sample, support rack and cover are allowed to drain vertically for 60±5 seconds, taking care not to excessively shake or vibrate the sample. While the sample is draining, the rack cover is carefully removed and all excess water is wiped from the support rack. The wet sample and the support rack are weighed on the previously tared balance. The weight is recorded to the nearest 0.01 g. This is the wet weight of the sample.

The procedure is repeated for with another sample of the fibrous structure, however, the sample is positioned on the support rack such that the sample is rotated 90° compared to the position of the first sample on the support rack.

The gram per fibrous structure sample absorptive capacity of the sample is defined as (wet weight of the sample–dry weight of the sample). The calculated VFS is the average of the absorptive capacities of the two samples of the fibrous structure.

Dimensions of Linear Element/Linear Element Forming Component Test Method

The length of a linear element in a fibrous structure and/or the length of a linear element forming component in a molding member is measured by image scaling of a light microscopy image of a sample of fibrous structure.

A light microscopy image of a sample to be analyzed such as a fibrous structure or a molding member is obtained with a representative scale associated with the image. The images is saved as a *.tiff file on a computer. Once the image is saved, SmartSketch, version 05.00.35.14 software made by Intergraph Corporation of Huntsville, Ala., is opened. Once the software is opened and running on the computer, the user clicks on "New" from the "File" drop-down panel. Next, "Normal" is selected. "Properties" is then selected from the "File" drop-down panel. Under the "Units" tab, "mm" (millimeters) is chosen as the unit of measure and "0.123" as the precision of the measurement. Next, "Dimension" is selected from the "Format" drop-down panel. Click the "Units" tab and ensure that the "Units" and "Unit Labels" read "mm" and that the "Round-Off" is set at "0.123." Next, the "rectangle" shape from the selection panel is selected and dragged into the sheet area. Highlight the top horizontal line of the rectangle and set the length to the corresponding scale indicated light microscopy image. This will set the width of the rectangle to the scale required for sizing the light microscopy image. Now that the rectangle has been sized for the light microscopy image, highlight the top horizontal line and delete the line. Highlight the left and right vertical lines and the bottom horizontal line and select "Group". This keeps each of the line segments grouped at the width dimension ("mm") selected earlier. With the group highlighted, drop the "line width" panel down and type in "0.01 mm." The scaled line segment group is now ready to use for scaling the light microscopy image can be confirmed by right-clicking on the "dimension between", then clicking on the two vertical line segments.

To insert the light microscopy image, click on the "Image" from the "insert" drop-down panel. The image type is preferably a *.tiff format. Select the light microscopy image to be inserted from the saved file, then click on the sheet to place the light microscopy image. Click on the right bottom corner of the image and drag the corner diagonally from bottom-right to top-left. This will ensure that the image's aspect ratio will not be modified. Using the "Zoom In" feature, click on the image until the light microscopy image scale and the scale group line segments can be seen. Move the scale group segment over the light microscopy image scale. Increase or decrease the light microscopy image size as needed until the light microscopy image scale and the scale group line segments are equal. Once the light microscopy image scale and the scale group line segments are visible, the object(s) depicted in the light microscopy image can be measured using "line symbols" (located in the selection panel on the right) positioned in a parallel fashion and the "Distance Between" feature. For length and width measurements, a top view of a fibrous structure and/or molding member is used as the light microscopy image. For a height measurement, a side or cross sectional view of the fibrous structure and/or molding member is used as the light microscopy image.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A multi-ply fibrous structure that exhibits a CD TEA of greater than 8.7 cm-g/cm$^2$ as measured according to the TEA Test Method and a Dry Burst of less than 600 g as measured according to the Dry Burst Test Method.

2. The multi-ply fibrous structure according to claim 1 wherein the multi-ply fibrous structure exhibits a Dry Burst of greater than about 100 g as measured according to the Dry Burst Test Method.

3. The multi-ply fibrous structure according to claim 1 wherein the multi-ply fibrous structure exhibits a Dry Burst of from about 100 g to about 500 g as measured according to the Dry Burst Test Method.

4. The multi-ply fibrous structure according to claim 1 wherein the multi-ply fibrous structure exhibits a CD TEA of greater than about 8.8 cm-g/cm$^2$ as measured according to the TEA Test Method.

5. The multi-ply fibrous structure according to claim 1 wherein the multi-ply fibrous structure comprises cellulosic pulp fibers.

6. The multi-ply fibrous structure according to claim 1 wherein the multi-ply fibrous structure comprises a through-dried fibrous structure.

7. The multi-ply fibrous structure according to claim 1 wherein the multi-ply fibrous structure comprises an uncreped fibrous structure.

8. The multi-ply fibrous structure according to claim 1 wherein the multi-ply fibrous structure exhibits a basis weight of greater than 15 gsm to about 120 gsm as measured according to the Basis Weight Test Method.

9. The multi-ply fibrous structure according to claim 1 wherein the multi-ply fibrous structure is a multi-ply sanitary tissue product.

10. The multi-ply fibrous structure according to claim 9 wherein the multi-ply sanitary tissue product is in roll form.

11. The multi-ply fibrous structure according to claim 9 wherein the multi-ply sanitary tissue product is an absorbent towel.

12. The multi-ply fibrous structure according to claim 11 wherein the absorbent towel comprises at least one embossed fibrous structure ply.

13. The multi-ply fibrous structure according to claim 9 wherein the multi-ply sanitary tissue product is a toilet tissue.

14. The multi-ply fibrous structure according to claim 13 wherein the toilet tissue comprises at least one embossed fibrous structure ply.

15. The multi-ply fibrous structure according to claim 1 wherein the multi-ply fibrous structure comprises at least one embossed fibrous structure ply.

16. A multi-ply fibrous structure that exhibits a CD TEA of greater than 8 cm-g/cm$^2$ as measured according to the TEA Test Method and a Dry Burst of from about 100 g to about 600 g as measured according to the Dry Burst Test Method.

17. The multi-ply fibrous structure according to claim 16 wherein the multi-ply fibrous structure exhibits a CD TEA of greater than about 8.2 cm-g/cm$^2$ as measured according to the TEA Test Method.

18. The multi-ply fibrous structure according to claim 16 wherein the multi-ply fibrous structure exhibits a CD TEA of greater than about 8.5 cm-g/cm$^2$ as measured according to the TEA Test Method.

19. The multi-ply fibrous structure according to claim 16 wherein the multi-ply fibrous structure comprises cellulosic pulp fibers.

20. The multi-ply fibrous structure according to claim 16 wherein the multi-ply fibrous structure comprises at least one throughdried fibrous structure ply.

21. The multi-ply fibrous structure according to claim 16 wherein the multi-ply fibrous structure comprises at least one uncreped fibrous structure ply.

22. The multi-ply fibrous structure according to claim 16 wherein the multi-ply fibrous structure exhibits a basis weight of greater than 15 gsm to about 120 gsm as measured according to the Basis Weight Test Method.

23. The multi-ply fibrous structure according to claim 16 wherein the multi-ply fibrous structure comprises at least one embossed fibrous structure ply.

24. The multi-ply fibrous structure according to claim 16 wherein the multi-ply fibrous structure is a multi-ply sanitary tissue product.

25. The multi-ply fibrous structure according to claim 24 wherein the multi-ply sanitary tissue product is an absorbent towel.

26. The multi-ply fibrous structure according to claim 25 wherein the absorbent towel comprises at least one embossed fibrous structure ply.

27. The multi-ply fibrous structure according to claim 24 wherein the multi-ply sanitary tissue product is a toilet tissue.

28. The multi-ply fibrous structure according to claim 27 wherein the toilet tissue comprises at least one embossed fibrous structure ply.

29. The multi-ply fibrous structure according to claim 24 wherein the multi-ply sanitary tissue product is in roll form.

* * * * *

UNITED STATES PATENT AND TRADEMARK OFFICE
CERTIFICATE OF CORRECTION

| | | |
|---|---|---|
| PATENT NO. | : 7,704,601 B2 | Page 1 of 1 |
| APPLICATION NO. | : 12/040733 | |
| DATED | : April 27, 2010 | |
| INVENTOR(S) | : John Allen Manifold et al. | |

It is certified that error appears in the above-identified patent and that said Letters Patent is hereby corrected as shown below:

In Col. 19, line 43, the word "Are" should be Area

Signed and Sealed this
Fourth Day of January, 2011

David J. Kappos
*Director of the United States Patent and Trademark Office*